United States Patent [19]
Hopper et al.

[11] Patent Number: 5,399,721
[45] Date of Patent: Mar. 21, 1995

[54] SYNTHESIS OF OPTICALLY PURE 4-ARYL-2-HYDROXYTETRONIC ACIDS

[75] Inventors: Allen T. Hopper; Donald T. Witiak, both of Madison, Wis.

[73] Assignee: The Ohio State University Research Foundation, Columbus, Ohio

[21] Appl. No.: 201,775

[22] Filed: Feb. 25, 1994

Related U.S. Application Data

[60] Continuation-in-part of Ser. No. 847,295, Mar. 6, 1992, Pat. No. 5,298,526, which is a division of Ser. No. 464,511, Jan. 12, 1990, Pat. No. 5,095,126.

[51] Int. Cl.[6] .............................................. C07D 307/62
[52] U.S. Cl. ..................................... 549/315; 549/60; 549/316
[58] Field of Search ....................... 549/60, 315, 316; 514/444, 473, 474

[56] References Cited

U.S. PATENT DOCUMENTS

| | | | |
|---|---|---|---|
| 5,008,405 | 4/1991 | Hatanaka et al. | 549/315 |
| 5,095,126 | 3/1992 | Witiak et al. | 549/315 |
| 5,298,526 | 3/1994 | Witiak et al. | 514/473 |

OTHER PUBLICATIONS

Ando, *J. Chem. Soc. Japan*, 1935, 56:745–756.
Belletire et al., "Dealkylative Decarboxylation, IV[1]. A Novel Approach to Ketene Thioacetals", *Tetrahedron Lett.*, 1984, 25(50):5729:5732.
Bloomer et al., "Total Synthesis of a γ-Carboxymethyltetronic Acid", *J. Org. Chem.*, 1974, 39:113–125.
Bodansky, *Principles of Peptide Syn.*, Springer-Verlag, Berlin, N.Y., 1984, p. 160.
Booth et al., "Preparation of Acyltetronic Acids using t-Butyl Acetothioacetate: Total Synthesis of the Fungal Metabolites Carolic, Carlosic, and Carlic Acids", *J. Chem. Soc. Perkin Trans I*, 1987, 121–127.
Brandange et al., "Studies on the Intramolecular Claisen Condensation; Facile Synthesis of Tetronic Acids", *J. Org. Chem.*, 1984, 49:927–728.
Compere, "Synthesis of α-Hydroxyarylacetic Acids from Bromoform, Arylaidehydes, and Potassium Hydroxide, with Lithium Chloride Catalyst", *J. Org. Che.*, 1968, 33:2565–2566.
Corey et al., "Oxidative Hydrolysis of 1,3–Dithiane Derivatives to Carbonyl compounds Using N–Halosuccinimide Reagents", *J. Org. Chem.*, 1971, 36:3553.
Eaborn, "The Interaction of Phenacyl Chloride and Aqueous Alkali", *J. Chem. Soc.*, 1957, pp. 1935–1936.
Evans et al., "The Asymmetric Synthesis of α–Amino and α–Hydrazino Acid Derivatives via The Stereoselective Amination of Chiral Enolates with Azodicarboxylate Esters", *Tetrahedron*, 1988, 44:5525–5540.
Gore et al., "Oxidation of Enolates by Dibenzyl Peroxydicarbonate to Carbonates of α–Hydroxy Carbonyl Compounds", *J. Org. Chem.*, 1986, 51:3700–3704.
Haynes et al., "Tetronic Acids", *Quart. Rev.*, 1960, pp. 292–315.
Helferich et al., "Eine neue Ascorbinsäure-Synthese", *Ber.*, 1937, 70:465–468.
Ireland et al., "Approach to the Total Synthesis of Chlorothricolide: Synthesis of (+)-19,20-Dihydro-2-4-O-methylchlorothricolide, Methyl Ester, Ethyl Carbonate", *J. Org. Chem.*, 1986, 51:635–648.
Ireland et al., "An Approach to the Total Synthesis of Chlorothricolide: The Synthesis of the Top Half", *J. Org. Chem.*, 1979, 44:3041–3052.
Kamanna et al., "Serum Lipoprotein and Apoprotein Concentrations in 4-(4-Chlorophenyl)-2-Hydroxytentronic Acid and Clofibate-treated Cholesterol and Cholic Acid-fed Rats", *Lipids*, 1989, 24:25–32.

(List continued on next page.)

Primary Examiner—Richard L. Raymond
Attorney, Agent, or Firm—Klauber & Jackson

[57] ABSTRACT

The present invention relates to a method for synthesis of optically pure stereogenically labile 4-aryl-2-hydroxytetronic acids from an optically pure aldehyde. The invention further relates to the use of such optically pure compounds as potent inhibitors of platelet aggregation by working at the level of cyclooxygenase. the invention further relates to the pharmaceutical use of such compounds in the treatment of coronary artery diseases, especially in the treatment and/or prevention of atherosclerosis.

10 Claims, No Drawings

OTHER PUBLICATIONS

Shank, "Reductones," *Synthesis,* 1972, pp. 176–190.

Stork et al., "Iterative Butnolide Construction of Polypropionate Chains", *J. Am. Chem. Soc.,* 1987, 109:1564–1565.

Whitesell et al., "Resolution of Chiral Alcohols with Mandelic Acid", *J. Org. Chem.,* 1983, 48:3548–3551.

Witiak and Tehim, "Synthetic Approaches to 4-Spiro-2-hydroxytetronic Acids", *J. Org. Chem.,* 1987, 52:2324–2327.

Witiak and Tehim, "Efficient Syntheses for Optically Pure Sterogenically Labile 4-Substituted-2-hydroxytetronic Acid", *J. Org. Chem.,* 1990, 55:1112–1114.

Witiak et al., "Synthetic aci–Reductones: 3,4–Dihydroxy-2-H-1-benzopyran-2-ones and Their cis-and trans-4a, 5,6,7,8,8a-Hexahydro Diastereomers. Antiaggregatory, Antillipidemic, and Redox Properties Compared to Those of the 4–Substituted 2-Hydroxytetronic Acids", *J. Med. Chem.* 1988, 31:1434–1445.

Witiak et al., "Hypocholesterolemic and Antiaggregatory Properies of 2-Hydroxytetronic Acid Redox Analogues and their Relationship to Clofibric Acid", *J. Med. Chem.,* 1982, 25:90–93.

Wrobel et al., "Total Syntheisi of (−)-Vertinolide. A General Approach to Chiral Tetronic Acids and Butenolides from Allylic Alcohols", *J. Org. Chem.,* 1983, 48:3761–3764.

SYNTHESIS OF OPTICALLY PURE 4-ARYL-2-HYDROXYTETRONIC ACIDS

This invention was made with Government support under Grant No. NCI-2T32CA09498 awarded by the U.S. Public Health Service National Heart, Lung and Blood Institute. The Government has certain rights in this invention.

This Application is a Continuation-In-Part of U.S. Ser. No. 07/847,295, filed Mar. 6, 1992, now U.S. Pat. No. 5,298,526; which is a division of U.S. Ser. No. 07/464,511, filed Jan. 12, 1990, and now U.S. Pat. No. 5,095,126.

BACKGROUND OF THE INVENTION

The present invention relates generally to methods for the synthesis of optically pure 4-aryl-2-hydroxytetronic acid aci-reductone compounds.

The aci-reductone 4-(4-chlorophenyl)-2-hydroxytetronic acid compound (CHTA) of the formula

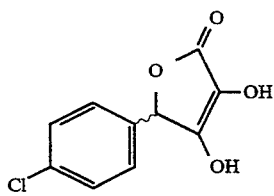

possesses antilipidemic and antiaggregatory properties which differ from those of the classical phenoxyactetic acids as has been disclosed in Witiak et al. *J. Med. Chem.*, 1988, 31:1434–1445 and Kamanna et al., *Lipids*, 1989, 24:25–32. Although unsubstituted-, 2-alkyl- and 2-acyltetronic acids are frequently found in nature, the 2-hydroxy substituted redox system is found only in vitamin C and its closely related relatives (isoascrobic acid, erythroascorbic acid) and derivatives, and the macrolide antibiotic chlorothricin.

The antiaggregatory activities of 2-hydroxytetronic acid aci-reductone compound (CHTA) is of interest since blood platelets are involved in the genesis of atherosclerosis. 2-Hydroxytetronic acid aci-reductones inhibit collagen-induced human platelet aggregation and secretion of [$^{14}$C]-serotonin in a concentration-dependent manner at equivalent doses, as reported in Witiak et al., *J. Med. Chem.*, 1982, 25:90–93. The CHTA compound inhibits platelet function by a similar mechanism, involving arachidonic acid release. Redox analogues, such as 2-hydroxytetronic acid, function as antioxidants in membranes or interfere with free radical processes involved in the biosynthetic elaboration of cyclic prostaglandin endoperoxides (PGG$_2$ and PGH$_2$), and, subsequently, thromboxane A$_2$ from arachidonic acid.

The synthesis of 4-aryl-2-hydroxytetronic acid compounds of the present invention is complicated by the stereochemical lability of the C-4 stereogenic center. The lability of this center in tetronic acids can be compared to the lability of the asymmetric center of mandelic acid; Whitesell et al., *J. Org. Chem.*, 1983, 48.:3548–3551 and Gore et al., *J. Org. Chem.*, 1986, 51:3700–3704, and phenylglycine, Evans et al., *Tetrahedron*, 1988, 44:5525–5540, Bodansky, *Principles of Peptide Syn.*, Springer-verlag, Berlin, N.Y., 1984, p. 160, which discloses that phenylglycine undergoes extensive racemization during peptide synthesis.

Older synthetic methods such as disclosed in Helferich et al., *Ber.*, 1937, 70:465–468, involving benzoin and intermolecular Claisen condensations employed in the synthesis of L-ascorbic acid, produce racemic 4-aryl-2-hydroxytetronic acids. Various syntheses published for the naturally occurring chiral tetronic acids such as (−)-vertinolide (Wrobel et al., *J. Org. Chem.*, 1983, 48:3761–3764); (S)-carlosic acid (Bloomer et al., *J. Org. Chem.*, 1974, 39:113–125); chlorothricin (Ireland et al., *J. Org. Chem.*, 1986, 51:635–648); related 2-acylated (Booth et al., *J. Chem. Soc. Perkin Trans I*, 1987, 121–129; or 2-unsubstituted (Brandange et al., *J. Org. Chem.*, 1984, 49, 927–928) tetronic acids, and chiral tetronic acid intermediates useful for the synthesis of the seco acid of erthronolide B (Stork et al., *J. Am. Chem. Soc.*, 1987, 109:1564–1565), were not applicable for the synthesis of optically pure enantiometers of 4-aryl-2-hydroxytetronic acids. Some targets contain quaternary chiral centers not expected to undergo racemization during their preparation as disclosed in Wrobel et al., supra, and Ireland et al., supra.

Syntheses for 2-hydroxytetronic acids other than ascorbic acid have been reviewed by Haynes and Plimmer in "Tetronic Acids," *Quart. Rev.*, pp. 292–315 (1960), and by Shank, "Reductones," *Synthesis* pp. 176–90 (1972). 2-Hydroxytetronic acids have generally been prepared using three different routes: (1) hydroxyl group insertion at the 2 position of the corresponding tetronic acid nucleus; (2) intramolecular Claisen cyclization of substituted glyoxylate esters; and (3) base-promoted cyclization of 2,4-dihydroxy-3-ketobutanoates.

Witiak and Tehim, *J. Org. Chem.*, 52:2324–2327 (1987) have synthesized the 5- and 6-membered spiro 2-hydroxytetronic acids using propargyl alcohol conversion to methyl tetronate by treatment with sodium methoxide. Attempted hydroxylation at the 2-position by α-lithiation and reaction with dibenzoylperoxide provided only a 6% yield of the corresponding 2-benzoyloxytetronic acid. However, the 2-hydroxyl group was introduced in good yields by lithiation using lithium diisopropylamide (LDA), boronate ester formation [B(MeO)$_3$] and oxidative hydrolysis (AcOH, H$_2$O$_2$). Methyl 2-hydroxytetronate was converted to the corresponding aci-reductone by stirring in 48% HBr at 45° C. for 12 hours. Ireland and Thompson, *J. Org. Chem.*, 44:3041–3052 (1979), have utilized the Claisen condensation for construction of 2-hydroxytetronic acids.

Witiak and Tehim, *J. Org. Chem.*, 52:2324–2327 (1987) have also prepared 5- and 6-membered spiro-2-hydroxytetronic acids using strategies developed by Ireland and Thompson, supra. This method was superior to use of hydroxyl group insertion methods because fewer steps were necessary and overall yields were higher. For example, Claisen cyclization of easily prepared methoxy or benzyloxy thiocarboxylate intermediates using LDA or lithium hexamethyldisilazide (LiHMDA) at −78° C. occurred in high yields. The resultant 2-methoxytetronic acids underwent deprotection by acetylation and subsequent reaction with BBr$_3$, whereas the 2-benzyloxytetronic acids were convertible to target 2-hydroxytetronic acid by transfer hydrogenation.

Witiak and Tehim, *J. Org. Chem.*, 55.:1112–1114 (1990), developed the first synthesis for optically pure (S)-(+)-4-phenyl-2-hydroxytetronic acid using the Claisen cyclization under kinetically controlled conditions. The 2-benzyloxyacetate derivative of the corresponding methyl mandelate underwent such cyclization at −100° C. using the sterically hindered non-nucleophilic base, lithium dicyclohexylamide (LiDCyA). Subsequent benzyl group deprotection of the tetronic acid generated the desired compound in low overall yields; 12% for both steps.

Parent Application Serial Nos. 07/464,511 (now U.S. Pat. No. 5,095,126) and 07/847,295 (now U.S. Pat. No. 5,298,526) relate to the preparation of optically pure stereogenically labile 4-substituted-2-hydroxytetronic acid compounds.

SUMMARY OF THE INVENTION

The present invention relates to a method for the synthesis of optically pure 4-aryl-2-hydroxytetronic acids containing electron withdrawing substituents. The chiral approach of the present invention utilizes an aldol condensation between optically pure α-t-butyldimethylsilyloxyarylacetaldehydes and the anion of ethyl 1,3-dithiane-2-carboxylate, followed by trapping the intermediate alkoxide anion with pivaloyl chloride to yield a fully protected butanoate ester containing the masked enediol functionality of the target aci-reductones. The dithiane moiety is then oxidatively hydrolyzed to produce an α-keto ester which undergoes fluoride anion catalyzed-cyclization to 2-pivaloyloxytetronic acid derivatives which are then hydrolyzed under acidic conditions or by hydride reduction to the corresponding 4-aryl-2-hydroxytetronic acids.

The invention is further related to the methods of using such optically pure compounds as potent inhibitors of platelet aggregation, and pharmaceutical compositions therefor.

The invention is further concerned with the pharmaceutical use of such compositions for the treatment and/or the prevention of coronary artery diseases, platelet aggregation and thrombosis, and/or prevention of atherosclerosis.

DETAILED DESCRIPTION OF THE INVENTION

In a first embodiment, the present invention relates to a process for making optically pure 4-aryl-2-hydroxytetronic acid compounds of Formula I:

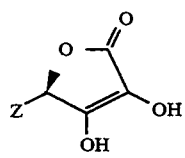
(Ia)

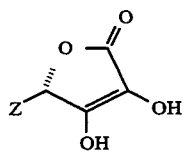
(Ib)

wherein Z is a substituted or unsubstituted aryl group.

This process comprises:
(a) reacting an optically pure aldehyde of the formula II

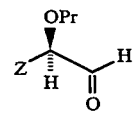
(II)

or its corresponding isomer, wherein Pr is a protecting group selected from the group consisting of t-butyldimethylsilyl, tetrahydropyranyl, thiomethyl, methoxymethyl, and Z is as hereinbefore defined, with the anion of an alkyl 1,3-dithiane-2-carboxylate followed by trapping of the intermediate alkoxide anion with a pivaloyl halide to yield a protected ester of the formula

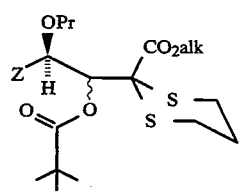
(III)

or its corresponding isomer, wherein Z and Pr are as hereinbefore defined and alk is a lower alkyl group;

(b) oxidatively hydrolyzing the protected ester of formula III to yield the α-keto ester of formula IV

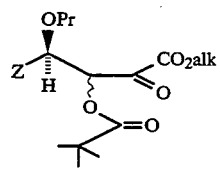
(IV)

or its corresponding isomer, wherein Z, Pr and alk are as hereinbefore defined;

(c) catalytically cyclizing the ester of formula IV to yield the 2-pivaloyloxytetronic acid derivative of formula V:

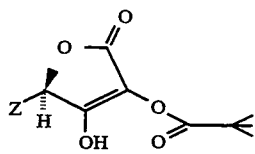
(V)

or its corresponding isomer, wherein Z is as hereinbefore defined; and (d) removal by hydrolysis or reductive cleavage of the pivaloyl ester group to afford the desired optically pure 4-aryl-2-hydroxytetronic acid of formula Ia or Ib.

Step (a) of the instant process utilizes as starting material, the appropriate optically pure hydroxy aldehyde of the formula

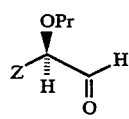
(II)

or its corresponding isomer, wherein Z and Pr are as hereinbefore defined which, in a 1:1.1 mixture with pivaloyl chloride, is reacted with the lithium salt of an alkyl 1,3-dithiane-2-carboxylate at about −78° C. in a nonpolar aprotic solvent such as tetrahydrofuran according to the method of Belletire et al., *Tetrahedron Lett.* 25(50):5729–5732 (1984). Preferably, the alkyl 1,3-dithiane-2-carboxylate is ethyl or methyl 1,3-dithiane-2-carboxlate, but other alkyl esters may similarly be utilized. The Pr protecting group is most preferably a t-butyldimethylsilyl (TBDMS) group, but other hydroxy protecting groups such as tetrahydropyranyl, methoxymethyl and thiomethoxy can be similarly utilized.

Thus afforded is the compound of formula III

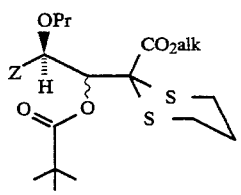

(III)

or its corresponding isomer, wherein Z, Pr and alk are as hereinbefore defined, which is then oxidatively hydrolyzed using N-chlorosuccinimide (NCS) and silver nitrate according to the method of Corey and Erickson, *J. Org. Chem.*, 36:3553 (1971). Typically, this hydrolysis is conducted at room temperature in an aqueous organic solvent, such as aqueous acetonitrile.

The resultant compound of formula IV, i.e.,

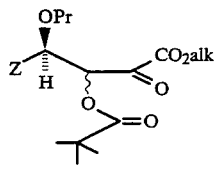

(IV)

or its corresponding isomer, wherein Z, Pr and alk are as hereinbefore defined, is then catalytically cyclized to yield the 2-pivaloyloxytetronic acid derivative of formula V:

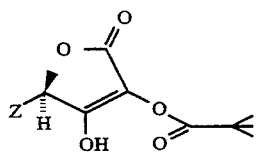

(V)

or its corresponding isomer, wherein Z is as hereinbefore defined.

The cyclization of step (c) is induced with tetrabutylammonium fluoride (TBAF) and is usually conducted with a non-polar aprotic solvent such as tetrahydrofuran or a similar ether. Typical reaction times vary from 5–20 minutes and the reaction is usually conducted at room temperature. Interestingly, the pivaloyl group undergoes O→O-acyl migration during the cyclization step (c).

Step (d) of the instant reaction sequence hydrolyzes the compound of formula V to afford the desired optically pure 4-aryl-2-hydroxytetronic acid of formulae Ia or Ib.

Typically, the hydrolysis of step (d) is accomplished with a mild aqueous acid, such as acetic acid, at reflux temperatures for 12–36 hours. A preferred hydrolysis utilizes 9.8:0.2 acetic acid:water for 24 hours at reflux temperatures. These conditions yield the target compound of formula I with minimal racemization.

Alternately, the pivoloate cleavage can be accomplished under neutral conditions by selective hydride reduction. In this alternate embodiment, the compound of formula V is dissolved in an organic solvent and preferably cooled to liquid nitrogen temperatures under a nitrogen atmosphere. This solution is then treated with, for instance, DIBAL-H to effect reductive cleavage of the pivaloyl ester.

A second embodiment of the present invention relates to optically pure 4-aryl-2-hydroxytetronic acid compounds of the general formulae Ia or Ib

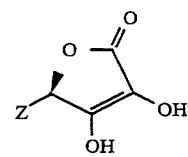

(Ia)

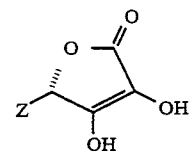

(Ib)

wherein Z is a substituted or unsubstituted aryl group.

In a composition aspect, the present invention encompasses novel pharmaceutical compositions comprising the optically pure compound of the general formulae Ia and Ib, together with a physiologically acceptable carrier or excipient, in an amount sufficient to have antilipidemic or antiaggregatory activities in an animal or patient. The compounds and their compositions of the present invention are thus useful in the treatment or prevention of atherosclerotic disorders.

As used herein, the term "substituted or unsubstituted aryl" means an organic, aromatic group which can be unsubstituted or substituted by one or more halogen, lower alkyl, alkoxy, aromatic or heteroaromatic groups. Examples of unsubstituted aryl groups include phenyl, pyridyl, thiophenyl, furyl, pyrrolyl and the like. Examples of substituted aryl groups include those such as halogen substituted phenyl, e.g., 4-chlorophenyl, 2,3-dichlorophenyl, 2,4-dichlorophenyl; alkyl-substituted aryl, e.g., tolyl, 3-methylpyridyl, 2,3-dimethylphenyl, 4-ethylphenyl; alkoxysubstituted aryl, e.g., 4-methoxyphenyl; and aryl-substituted aryl, e.g., 1,1'-biphenyl.

As used herein, the term "alkyl" means straight- or branched-chain saturated aliphatic hydrocarbon groups preferably containing 1–6 carbon atoms. Representative of such groups are methyl, ethyl, isopropyl, isobutyl, butyl, pentyl, hexyl and the like.

The term "alkoxy" means a lower alkyl group attached to the remainder of the molecule by oxygen. Examples of alkoxy are methoxy, ethoxy, propoxy, isopropoxy and the like.

The starting materials of formula II are known in the art and/or are preparable by methods described herein. Optically pure enantiomers of mandelic acid are commercially available. Numerous methods exist for the manufacture of optically active and optically pure derivatives of mandelic acid such as the p-chloro- and p-phenylmandelic acids. A wide range of chiral bases are used to resolve mandelic acid precursors including methylbenzylamine, brucine and ephedrine. Partial separation of enantiomers is accomplished with optically active solvents such as (−)-menthone, (−)-menthyl acetate and (+)-limonene. Anion-exchange chromatography using a chiral stationary phase constructed of 1-p-nitrophenyl-2-amino-1,3-propanediol, or chromatography through starch successfully separates mandelic acid enantiomers. Reduction of 1-menthyl benzoylformate with Na-amalgam followed by saponification of the menthyl ester provides 1-mandelic acid. Asymmetric syntheses of mandelic acid precursors include the Alpine borane reduction of methyl benzoylformate, hydroxy insertion using Evan's chiral imide enolate, and L-selectride reduction of (+)- or (−)-menthol benzoylformate.

Procedures developed for the production of racemic mandelic acid derivatives are well documented in the literature. Ando's scheme (Ando, *J. Chem. Soc. Japan*, 56:745-756 (19.35)) relies upon the condensation of benzene derivatives with ethyl ketomalonate in the presence of $SnCl_4$. This affords hydroxy diesters which after saponification and decarboxylation liberate racemic mandelic acid derivatives. The approach formulated by Compere (Compere, *J. Org. Chem.*, 33:2565-2566 (1968)) generates mandelic acid derivatives in one step and in high yield by condensing substituted benzaldehydes with bromoform in the presence of potassium hydroxide and lithium chloride. Furthermore, mandelic acid is obtained in 45% yield by subjecting α-chloroacetophenone to aqueous alkali under normal atmospheric conditions (see Eaborn, *J. Chem. Soc.,* pp. 1935-1936 (1957)).

A generally useful method involves the production of the optically pure (R) isomers of mandelic acid by resolution using R(+)-methylbenzyl amine and recrystallization of the salt from absolute ethanol. Typically, the compound of the formula VI

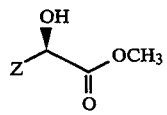

wherein Z is as hereinbefore defined, is obtained by washing an ether solution of the salt of the formula VII

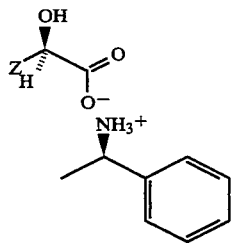

wherein Z is as hereinbefore defined, with 5% aqueous HCl. The ether layer is separated, cooled to 0° C. and titrated with $CH_2N_2$ to obtain the optically pure methyl ester of formula VI. This ester of formula VI is then converted to the necessary starting material of formula II by treatment with t-butyldimethylsilylchloride (TBDMSCl) and imidazole in dimethylformamide, followed by DIBAL-H reduction at −78° C.

The invention also provides for pharmaceutical compositions comprising the optically pure compounds of the general formula I above, as well as their physiologically acceptable salts (such as, for example, $Na^+$, $K^+$, $NH_4^+$).

The compounds of the invention have antilipidemic and antiaggregatory activity and are useful in the treatment or prevention of atherosclerotic disorders. The invention accordingly further provides optically pure compounds of the general formula I and their physiologically acceptable salts for use in the therapy or prophylaxis of atherosclerotic disorders.

When tested according to the methods described in the art, the (S)-isomers of formula I having the formula

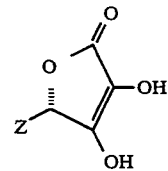

have been found to possess markedly superior properties when compared to their corresponding (R)-isomers.

The R- and S-enantiomers were tested as inhibitors of arachidonic acid-induced platelet aggregation in human platelet-rich plasma. Data for individual experiments (2 separate donors) are given as $pIC_{50}$ (log molar inhibitory concentration of each drug which blocks aggregation to arachidonic acid by 50%) Inhibitors were preincubated for 1 minute prior to addition of arachidonic acid (200–400 μM). Changes in light transmission were measured as an index of aggregation and quantified after 4 minutes.

These properties are summarized in Tables 1 and 2 below:

TABLE 1

| Data Set 1: | (R)-(−)-5-[(1,1'-biphenyl)4-yl]-3,4-dihydroxy-2(5H)-furanone | |
|---|---|---|
| Data Set 2: | (S)-(+)-5-[(1,1'-biphenyl)4-yl]-3,4-dihydroxy-2(5H)-furanone | |
| Data Set 1 | | Data Set 2 |
| 3.670 | | 4.609 |
| 3.796 | | 6.614 |
| 4.592 | | 8.699 |
| 4.910 | | 5.495 |
| 3.636 | | 4.733 |
| 4.121 | AVE | 6.030 |
| 0.589 | STD | 1.693 |
| 0.263 | SEM | 0.757 |
| 14.293 | C V | 28.062 |
| 5 | N | 5 |
| 3.390 | −95% CL | 3.929 |
| 4.852 | +95% CL | 8.131 |

Paired T = 2.843609
Degree of freedom = 4
p = 0.046697*

TABLE 2

| Data Set 1: | (R)-(−)-5-(p-chlorophenyl)-3,4-dihydroxy-2(5H)-furanone | |
|---|---|---|
| Data Set 2: | (S)-(+)-5-(p-chlorophenyl)-3,4-dihydroxy-2(5H)-furanone | |
| Data Set 1 | | Data Set 2 |
| 3.575 | | 4.654 |
| 3.446 | | 5.699 |
| 3.511 | AVE | 5.176 |
| 0.091 | STD | 0.739 |
| 0.065 | SEM | 0.523 |
| 2.604 | C V | 14.280 |
| 2 | N | 2 |
| 2.689 | −95% CL | −1.465 |

TABLE 2-continued

| | | |
|---|---|---|
| 4.332 | +95% CL | 11.817 |

Paired T = 2.836126
Degree of freedom = 1
p = 0.215804 (not significant)
Try + 2 replicates/set The compounds of the invention may be formulated in a conventional manner, optionally together with one or more other active ingredients, for administration by any convenient route for example of oral, intravenous or intramuscular administration.

Thus, according to another aspect, the invention provides a pharmaceutical composition comprising a compound of formula I and/or a pharmaceutically acceptable salt thereof together with a pharmaceutically acceptable carrier or excipient.

For oral administration, the pharmaceutical composition may take the form of, for example, tablets, capsules, powders, solutions, syrups or suspensions prepared by conventional means with physiologically acceptable excipients.

The compounds may be formulated for intravenous or intramuscular administration in dry form for reconstitution before use, or as a sterile solution or suspension.

A proposed daily dose based on similar pharmokinetic parameters to CHTA for administration to man is 10 to 25 mg/kg, for example 1 gm daily to 70 kg, which may be conveniently administered in 1 to 3 doses per day. The precise dose administered will, of course, depend on the age and condition of the patient.

The following examples illustrate the present invention.

Melting points were determined in open capillaries with a Thomas-Hoover Uni-Melt Apparatus and are uncorrected. Infrared spectra were recorded by a Laser Precision Analytical RFX-FTIR spectrometer (model TSI-400). Nuclear magnetic resonance spectra were obtained with either an IBM-Bruker model NR/250 or NR/270 FT NMR spectrometer. Tetramethylsilane (TMS) in $CDCl_3$, $DMSO-d_6$, $acetone-d_6$, $CD_3OD$ or $D_2O$ was used as internal standard. Chemical shifts were reported on the δ scale with peak multiplicities: s, singlet; d, doublet; dd, doublet of doublets; ddd, doublet of doublets of doublets; t, triplet; q, quartet; m, multiplet. Tetrahydrofuran (THF) was distilled from Na/-Benzophenone ketyl; $CH_2Cl_2$ was dried over $P_2O_5$; and DMF was distilled and stored over molecular sieves. Optical rotations were taken on a Perkin-Elmer model 241 polarimeter using a 10 cm, 1 mL cell. Mass spectra were acquired with either a Kratos MS25RFA or a VG 70-250S mass spectrometer. Elemental analyses were performed by Galbraith Laboratories, Inc., Knoxville, Tenn.

PREPARATION OF STARTING MATERIALS

EXAMPLE A

Methyl p-chlorophenyl-α-hydroxyacetate

A. To a 2-necked 500 mL round bottom flask equipped with a condenser, nitrogen inlet and septum was added 35 g (250 mmol) of p-chlorophenylcarboxaldehyde, 49 g (750 mmol) of KCN, 0.3 g (2.5 mmol) of $Zn(CN)_2$, 135 mL of dry acetonitrile ($CH_3CN$) and 80 mL (625 mmol) of trimethylsilyl chloride (TMSCl). The suspension was warmed to reflux with stirring, and after 18 hours, an additional 35 mL (300 mmol) of TMSCl was added. The mixture was maintained at reflux for 18 hours, cooled, filtered (scintered glass), washed three times with 30 mL of acetonitrile ($CH_3CN$), and the combined filtrate was concentrated to a solid (Rotovap). The crude cyanohydrin was ground into a fine powder, diluted with 400 mL of concentrated HCl and stirred for 24 hours. The yellow suspension was poured onto 1500 g of ice, filtered, washed with several portions of $H_2O$ and dried leaving the crude acetamide, which may be recrystallized from THF and $CH_2Cl_2$: m.p. 120°–121° C.

The crude acetamide was dissolved in 600 mL of a 5M solution of KOH in methanol and warmed to reflux for 2 h, cooled to room temperature, concentrated, poured into 400 g of ice and acidified with 10% aqueous HCl. The suspension was extracted three times with 500 mL of $Et_2O$ and the combined $Et_2O$ extracts were washed once with 200 mL of $H_2O$ and extracted three times with 75 mL of $NaHCO_3$ solution. The combined $NaHCO_3$ extracts were washed twice with 50 mL of $Et_2O$, acidified with 10% aqueous HCl and extracted twice with 250 mL of $Et_2O$. The combined organic extracts were washed once with 75 mL of $H_2O$ and twice with 75 mL of brine, dried ($Na_2SO_4$) and concentrated to give p-chlorophenyl-α-hydroxyacetic acid, m.p. 98°–106° C., (lit m.p. 119°–120° C.).

B. A 250 mL round bottom flask containing 5.6 g (30 mmol) of p-chlorophenyl-α-hydroxyacetic acid and 100 mL of concentrated HCl:MeOH (1:9) was warmed to reflux for 12 hours. The solution was concentrated under reduced pressure, diluted with 250 mL of $Et_2O$ and washed once with 30 mL of $H_2O$, twice with 30 mL of $NaHCO_3$ solution, once with 30 mL of $H_2O$ and once with 30 mL of brine. The organic layer was dried ($Na_2SO_4$) and concentrated leaving 5.0 g (83%) of methyl p-chlorophenyl-α-hydroxyacetate lit m.p. 55° C.) $^1$H-NMR ($CDCl_3$) δ7.36–7.28 (m, 4H), 5.13 (s, 1 H), 3.72 (s, 3H), 3.67 (br s, 1 H (exchanges with $D_2O$)).

EXAMPLE B (R)-(−)-p-Chlorophenyl-α-hydroxyacetic acid

A. Selenium dioxide (35.5 g; 320 mmol) was dissolved in 250 mL of MeOH (warm to reflux with stirring), and 19.6 g (315 mmol) of α-bromo-4-chloroacetophenone was added. The reaction mixture was warmed to reflux for 24 hours, cooled, filtered and concentrated leaving an orange oil. The oil was diluted with 1500 mL of $Et_2O$ and washed three times with 200 mL of $H_2O$ and once with 200 mL of brine, dried ($Na_2SO_4$) and concentrated. The crude oil was crystallized from $Et_2O$ and hexanes at −20° C. The white needles were filtered while cold and washed with small portions of cold hexanes to yield 22 g (35%) of methyl p-chlorophenyl-α-oxoacetate, m.p. 56°–57° C., $^1$H-NMR ($CDCl_3$)δ8.0–7.9 (m, 2H), 7.5–7.4 (m, 2H), 3.9 (s, 3H); $^{13}$C-NMR ($CDCl^3$)δ184.4, 163.5, 141.6, 131.4, 131.0, 129.3, 52.7.

B. Methyl p-chlorophenyl-α-oxoacetate (16.0 g; 80 mmol) was dried under reduced pressure for 12 h in a 250 mL flask. The flask was filled with argon and 36 mL (120 mmol) of Alpine borane (prepared from (1R)-(+)-α-pinene of 93% ee) was added. The solid reaction mixture turned to a red suspension after 8 hours. The mixture was stirred and after 16 hours was cooled to 0° C. Acetaldehyde (6.7 mL) was added, with stirring. All volatile materials were removed by distillation (80° C., 0.3 mmHg), and the resultant orange oil was taken up in 200 mL of $Et_2O$ and cooled to 0° C. Ethanolamine (8 mL; 135 mmol) was added. The reaction mixture was stirred vigorously for 30 minutes, filtered (scintered glass packed with celite) and washed three times with 25 mL of Et$_2$O. The combined filtrate was washed once with 50 mL of H$_2$O and twice with 30 mL of brine, dried (Na$_2$SO$_4$) and concentrated leaving an orange oil.

The resultant crude hydroxyacetate was dissolved in 325 mL of MeOH, and 75 mL of an aqueous 0.42M solution of NaOH was added with stirring and at room temperature over a 2 hour period. After an additional 2 hours the solution was acidified to pH 6 with 10% aqueous HCl, concentrated under reduced pressure and diluted with 300 mL of H$_2$O and 75 mL of saturated NaHCO$_3$ solution. The solution was washed twice with 150 mL of Et$_2$O, acidified to pH 1 with 10% aqueous HCl and extracted three times with 150 mL of Et$_2$O. The Et$_2$O solution was washed once with 30 mL of H$_2$O and twice with 30 mL of brine, dried (Na$_2$SO$_4$) and concentrated leaving 12.5 g (84%) of the title optically active acid, 72% ee, $\alpha_D^{22} -96.12°$ (MeOH).

(S)-(+)-p-Chlorophenyl-α-hydroxyacetic Acid was synthesized by a nearly identical procedure as described for the corresponding (R)-(−)-enantiomer. The only difference was that the reduction was performed with Alpine borane prepared from (1S)-(−)-α-pinene of 98% ee.

(R)-(+)-Methylbenzylamine salt of (R)-(−)-p-Chlorophenyl-α-hydroxyacetic Acid The 72% ee acid (12.5 g; 67 mmol) was dissolved in 250 mL of absolute EtOH and warmed to reflux on a steam bath. (R)-(+)-Methylbenzylamine (8.6 mL; 67 mmol) was added and the flask was removed from the steam bath, seeded with a small crystal of the salt, wrapped in cotton and not disturbed for 48 hours. The crystals were filtered, washed six times with 25 mL portions of cold absolute EtOH and dried leaving 14.65 g (71%, 83% based on 72% ee) of the diastereomeric salt. The salt was recrystallized twice from EtOH to yield 12.5 g of the diastereomerically and optically pure title salt: m.p. 194°–200° C., $\alpha_D^{22} -49.7°$ (c=0.316,MeOH), $\alpha^{22}_{Hg365} -190°$ (c=0.316, MeOH).

(S)-(−)-Methylbenzylamine Salt of (S)-(+)-p-Chlorophenyl-α-hydroxyacetate was prepared as described for the corresponding (R)-(−)-enantiomer: m.p. 194°–200° C.; $\alpha_D^{22}+48.7°$ (c=0.624, MeOH), $\alpha^{22}_{Hg365}$ +185 (c=0.624, MeOH).

(R)-(−)-p-Chlorophenyl-α-hydroxyacetic Acid:

The (R)-(−)-amine salt (4.6 g; 15 mmol) was added to a separatory funnel containing 150 mL of Et$_2$O and 40 mL of 5% aqueous HCl and shaken vigorously until the salt dissolved. The Et$_2$O layer was separated and washed once with 25 mL of 5% aqueous HCl, twice with 25 mL of H$_2$O and once with 25 mL of brine, dried (Na$_2$SO$_4$) and concentrated leaving 2.7 g (97%) of the optically pure α-hydroxyacetic acid. For analytical data, a small sample was recrystallized as white needles from CH$_2$Cl$_2$ and pet ether: m.p. 117°–119° C. (lit m.p. 120.5°–121° C.); $\alpha_D^{22} -129°$ (c=0.966, EtOH).

(S)-(+)-p-Chlorophenyl-α-hydroxyacetic Acid was prepared as described for the corresponding (R)-(−)-enantiomer: m.p. 116°–119° C.; $\alpha_D^{22}+132°$ (c=1.42, EtOH)

EXAMPLE C (R)-(−)-Methyl p-Chlorophenyl-α-hydroxyacetate

A solution of (R)-(−)-p-chlorophenyl-α-hydroxyacetic acid (2.6 g; 14 mmol) in 100 mL of Et$_2$O was cooled to 0° C. and titrated with CH$_2$N$_2$ until the yellow color of CH$_2$N$_2$ persisted. Evaporation of solvent provided 2.65 g (96%) of the desired methyl ester as a colorless oil: $\alpha_D^{22} -110°$ (c=1.102, EtOH ).

(S)-(+)-Methyl p-Chlorophenyl-α-hydroxyacetate was prepared as described for the corresponding (R)-(−)-enantiomer: $\alpha_D^{22}+103°$ (c=1.555, EtOH).

EXAMPLE D (R)-(−)-Methyl p-Chlorophenyl-α-[((1,1-dimethylethyl) dimethylsilyl)oxy]-acetate (R)-(−)-methyl p-chlorophenyl-α-hydroxy acetate (2.05 g; 10.0 mmol), 2.26 g (15.0 mmol) of TBDMSCl, 1.09 g (16.0 mmol) of imidazole and 10 mL of DMF were combined in a 100 mL round bottom flask and stirred under argon for 18 hours. The reaction mixture was diluted with 150 mL of Et$_2$O, washed three times with 25 mL of H$_2$O and once with 25 mL of brine, dried (Na$_2$SO$_4$), and concentrated. The compound was dried under reduced pressure (0.3 mm Hg, 60° C.) for 1.5 hours to yield 3.03 g (97%) of the title tert-butyldimethylsilyloxyacetate as a colorless oil: $\alpha_D^{22} -60°$ (c=0.616, EtOH); $^1$H-NMR (CDCl$_3$)δ7.41–7.37 (m, 2H), 7.32–7.27 (m, 2H), 5.18 (s, 1H), 3.66 (s, 3H), 0.89 (s, 9H), 0.09 (s, 3H), 0.02 (s, 3H).

(S)-(+)-Methyl p-Chlorophenyl-α-[((1,1-dimethylethyl)dimethylsilyl)oxy]-acetate was prepared as described for the corresponding (R)-(−)-enantiomer: $\alpha_D^{22}$59° (c=0. 652, EtOH).

EXAMPLE E (R)-(−)-p-Chlorophenyl-α-[((1,1-dimethylethyl) dimethylsilyl)oxy]-acetaldehyde To a 100 mL 2-necked round bottom flask equipped with a septum and nitrogen inlet was added 3.0 g (9.5 mmol) of the (R)-(−)-methyl acetate prepared in Example D dissolved in 55 mL of dry toluene. The solution was cooled to −78° C. (CO$_2$/acetone) and 12 mL (12 mmol) of a 1.0M solution of DIBAL-H in toluene was added slowly (5 minutes) with stirring. The reaction mixture was stirred for 1 hour at −78° C. and poured into 100 g of ice and 100 mL of CHCl$_3$. The reaction flask was rinsed with 100 mL of CHCl$_3$ and the mixture was stirred vigorously for 30 minutes. After separation of the CHCl$_3$ layer, the aqueous phase was washed with 100 mL of CHCl$_3$ and the combined CHCl$_3$ extracts were washed once with brine 80 mL, dried (Na$_2$SO$_4$) and concentrated leaving 2.5 g (93%) of the title aldehyde as a clear colorless oil of better than 95% purity ($^1$H-NMR). The aldehyde was not further purified owing to its instability to temperatures above 60° C. and to silica gel: $\alpha_D^{22} -33.71°$ (c=0.330, EtOH); $^1$H-NMR (CDCl$_3$)δ9.47 (d, J=2.0 Hz, 1H), 7.33–7.32 (m, 4H), 4.95 (d, J=2.0 Hz, 1H), 0.92 (s, 9H), 0.10 (s, 3H), 0.02 (s, 3H).

(S)-(+)-p-Chlorophenyl-α-[((1,1-dimethylethyl) dimethylsilyl)oxy]-acetaldehyde was prepared as described for the corresponding (R)-(−)-enantiomer: $\alpha_D^{22}+46.5°$ (c=0.316, EtOH).

EXAMPLE F

[(1,1'-Biphenyl)4-yl]-α-hydroxyacetamide

To a 25 mL-round bottom flask containing a reflux condenser fitted with a nitrogen inlet and 3.0 g (16.5 mmol) of 4-biphenylcarboxaldehyde was added 3.21 g (49.4 mmol) of KCN, 0.019 g (0.16 mmol) of $Zn(CN)_2$, 9 mL of $CH_3CN$ and 3.1 mL (40.3 mmol) of TMSCl. The reaction mixture was warmed to reflux under $N_2$ with stirring for 20 h and an additional 2 mL (26 mmol) of TMSCl was added. The mixture was maintained at reflux for 10 h, cooled to room temperature and filtered through a scintered glass funnel. The KCN filter cake was washed twice with 5 mL portions of $CH_3CN$ and the combined filtrate was concentrated (Rotavap) to a yellow solid. The solid was ground to a powder and diluted with 40 mL of concentrated HCl and stirred for 20 hours. The pink-orange suspension was poured over ice (100 g) and filtered leaving 3.6 g (96%) of the title crude acetamide. Recrystallization from $THF:CH_2Cl_2$ left 3.0 g (80%) of the title acetamide as light yellow flakes: m.p. 225°-227° C. $^1H$-NMR $(CD_3OD)\delta 7.62-7.52$ (m, 6H), 7.44-7.31 (m, 3H), 5.04, (s, 1H)

EXAMPLE G

[(1,1'-Biphenyl)4-yl]-α-hydroxyacetic Acid

To a solution of 2.7 g (11.9 mmol) of the α-hydroxyacetamide prepared in Example F in 67 mL of MeOH was added 17 g of KOH, and the solution was warmed to reflux for 1 hour. The reaction mixture was cooled to room temperature and concentrated (Rotavap), poured into 20 g of crushed ice and acidified with 10% aqueous HCl. The precipitate (hydroxy acid) thus obtained was filtered, washed with small portions of $H_2O$, dried and recrystallized from $EtOH-H_2O$ as white crystals: m.p. 200-201 (lit. m.p. 201°-203° C.).

EXAMPLE H

Methyl α-[(1,1'-Biphenyl)4-yl]-α-hydroxyacetate

A 250 mL R. B. flask containing a condenser, drying tube, and 7.5 g (32.8 mmol) of the α-hydroxyacetic acid of Example G dissolved in 150 mL of concentrated HCl:MeOH (1:9) was warmed to reflux for 2 hours. The solution was concentrated under reduced pressure, and the residue was dissolved in 250 mL of $Et_2O$. The $Et_2O$ solution washed once with 50 mL of $H_2O$, twice with 50 mL portions of 10% $NaHCO_3$ solution, twice with 30 mL of $H_2O$ and twice with 30 mL of brine, dried ($MgSO_4$) and concentrated. The crude methyl acetate was recrystallized from EtOAc and Hexanes leaving 6.5 g (82%) of the title acetate: $^1H$ NMR ($CDCl_3$) $\delta 7.63-7.32$ (m, 9H), 5.22 (d, broad, 1H), 3.78 (s, 3H), 3.45 (d, broad, 1H).

EXAMPLE I

Methyl α-[(1,1'-Biphenyl)4-yl]-α-oxoacetate:

Method A: To a 100 mL round bottom flask with attached drying tube was added 2.42 g (10.0 mmol) of the methyl α-hydroxyacetate of Example H, 1.84 g (12 mmol) of pyridinium chlorochromate (PCC) and 70 mL of $CH_2Cl_2$. The suspension was stirred at room temperature for 24 hours. An additional 1.0 g (7 mmol) of PCC was added and stirring continued for 20 h. The reaction was quenched by the addition of 15 mL of $Et_2O$, filtered and concentrated under reduced pressure. Filtration over silica gel (70-230 mesh) using $CHCl_3:MeOH$ (97:03) as elutant produced a yellow oil which crystallized upon standing leaving 1.85 g (77%) of the title α-keto ester.

Method B: To a 100 mL R. B. flask with 1.9 g (7.8 mmol) of the methyl α-hydroxyacetate of Example H dissolved in 50 mL of acetone at 15° C. was added Jones reagent (chromic acid solution) with stirring at a rate to maintain the reaction temperature under 20° C. The reaction was monitored by TLC and after the disappearance of starting material 5 mL of iPrOH was added. The green chromium salts were removed by filtration, washed three times with 15 mL portions of acetone and the filtrate was concentrated. The crude mixture was diluted with 100 mL of $Et_2O$, and the $Et_2O$ solution was washed twice with 20 mL of $H_2O$ and twice with 20 mL of brine, dried ($MgSO_4$) and concentrated. Recrystallization from EtOAc and Hexanes provided 1.2 g (64%) of the title α-keto ester: m.p. 61°-62° C.; $^1H$-NMR $(CDCl_3)\delta 8.13-8.05$ (m, 2H), 7.74-7.62 (m, 4H), 7.53-7.44 (m, 3H), 3.98 (s, 3H).

EXAMPLE J

R-Methyl α-[(1,1'-Biphenyl)4-yl]-α-hydroxyacetate

To a 2-necked round bottom flask containing 2.4 g (10.0 mmol) of methyl α-[(1,1'-biphenyl)4-yl]-α-oxoacetate under $N_2$ was added 6 mL (20 mmol) of Alpine borane prepared from 92% ee (1R)-(+)-α-pinene. The reaction mixture was stirred at room temperature for 18 hours. The resultant off white solid was diluted with 3 mL of THF, cooled to 0° C. and 2 mL (35 mmol) of acetaldehyde was added. All volatile substances were removed by distillation (85° C. 0 3 mm Hg) and the intermediate boronate ester was diluted with 25 mL of $Et_2O$, cooled to 0° C. and hydrolyzed with 1.3 mL (22 mmol) of ethanolamine. The suspension was stirred for 30 min at 0° C., filtered through a celite packed scintered glass funnel and washed twice with 10 mL portions of $Et_2O$. The combined filtrate was washed once with 10 mL of $H_2O$ and twice with 10 mL of brine, dried ($MgSO_4$) and concentrated. R-methyl α-[(1,1'-biphenyl)4-yl]-α-hydroxyacetate was filtered through silica gel (70-230 mesh) using hexanes:EtOAc (90:10) as elutant and recrystallized from EtOAc and Hexanes to provide 1.1 g (46%) of the title optically active (R)-(−)-methyl acetate.

EXAMPLE K

Resolution of Racemic [(1,1'-Biphenyl)4-yl]-α-hydroxyacetic Acid with (R)-(+)-Methylbenzylamine and (S)-(−)-Methylbenzylamine.

The racemic acid of Example H (22.8 g; 100 mmol) was dissolved in 350 mL of absolute EtOH and warmed to reflux on a steam bath. (R)-(+)-Methylbenzylamine (12.8 mL; 100 mmol) was added, the flask removed from the steam bath, and the contents seeded with a small crystal of the salt. The flask was wrapped in cotton and not disturbed for 48 hours. The crystals were filtered, washed six times with 25 mL portions of cold absolute EtOH and dried leaving about 18 g of the crystalline salt. The salt was recrystallized three times using approximately 15 mL of ethanol for each gram of compound to yield 10 g [28% yield, 57% adjusted based on 50 mmol of (R)-acid] of the diastereomerically and optically pure salt of the title [(1,1'-biphenyl)4-yl]-α-hydroxyacetic acid: m p 196°-205° C., $\alpha_D^{22} -49.7°$ (c=0,306, MeOH).

The filtrate from the first recrystallization was concentrated and diluted with 500 mL of Et$_2$O. The Et$_2$O solution was washed three times with 50 mL of 10% aqueous HCl, twice with 50 mL of H$_2$O and twice with 50 mL of brine, dried (Na$_2$SO$_4$) and concentrated leaving 10 g (45 mmol) of the corresponding optically active (S)-(+)-hydroxy acid. The acid was dissolved in about 250 mL of absolute EtOH, the solution warmed to reflux, and 5.7 mL (45 mmol) of (S)-(−)-methylbenzylamine was added. The flask was wrapped in cotton and foil and set on a cork ring without disturbance for 48 hours. The crystals were filtered and washed with a minimum of cold EtOH. The salt was recrystallized 3 times using approximately 15 mL of EtOH for each 1 g of the diastereomeric salt leaving 8 g (23%, 46% adjusted) of: m.p. 197°–207° C.; $\alpha_D^{20}$ +44.2° (c=0.624,MeOH).

EXAMPLE L (R)-(−)-[(1,1'-Biphenyl)4-yl]-α-hydroxyacetic Acid:

(R)-(−)-Amine Salt (2.65 g; 7.6 mmol) was added to a separatory funnel containing 150 mL of Et$_2$O and 40 mL of 5% aqueous HCl, and the suspension was shaken vigorously until the salt dissolved. The Et$_2$O layer was separated and washed once with 25 mL of 5% aqueous HCl, twice with 25 mL of H$_2$O and once with 25 mL of brine, dried (Na$_2$SO$_4$) and concentrated leaving 1.7 g (98%) of optically pure (R)-(−)-[1,1'-biphenyl)4-yl]-α-hydroxyacetic acid. For analytical data, a small sample was recrystallized as white needles from THF and CH$_2$Cl$_2$: m.p. 210°–212° C.; $\alpha_D^{22}$ −135.2°(c=0.318, EtOH).

(S)-(+)-[](1,1'-Biphenyl)4-yl]-α-hydroxyacetic Acid was prepared as described for the corresponding (R)-(−)-enantiomer using the (S)-(+)-Amine salt prepared in Example K: m.p. 212°–215° C.; $\alpha_D^{22}$ +133.7° (c=0.662, EtOH)

EXAMPLE M (R)-(−)-Methyl [(1,1'-Biphenyl)4-yl]-α-hydroxyacetate

A solution of 1.7 g (7.5 mmol) of the (R)-(−)-p-phenylmandelic acid prepared in Example L in 75 mL of Et$_2$O was cooled to 0° C. and titrated with CH$_2$N$_2$ until the yellow color of CH$_2$N$_2$ persisted. Evaporation of solvent provided 1.8 g (99%) of the title methyl ester as a white crystalline solid: m.p. 103°–106° C.; $\alpha_D^{22}$ −121.0° (c=0.482, EtOH).

(S)-(+)-Methyl [(1,1'-Biphenyl)4-yl]-α-hydroxyacetate was prepared as described for the corresponding (R)-(−)-enantiomer: m.p 103°–106° C. $\alpha_D^{22}$+120.7° (c=0.372, EtOH).

EXAMPLE N

The Mosher Ester of Racemic Methyl [(1,1'-Biphenyl)4-yl]-α-hydroxyacetate

To a dry 10 mL round bottom flask equipped with a stir bar and 30 mg (0.13 mmol) of (R)-(+)-α-methoxy-α-(trifluoromethyl)phenylacetic acid [(R)-(+)-MTPA] under argon atmosphere was added 0.5 mL of oxalyl chloride containing 0.1% of DMF. The solution was stirred for 1 hour, and the excess oxalyl chloride was removed under reduced pressure (25° C., 0.3 mm Hg, 25 min). (R)-(−)-MTPA-Cl was placed under argon atmosphere and 12 mg (0.05 mmol) of racemic methyl [(1,1'-biphenyl)4-yl-α-hydroxyacetate, 0.2 mL of CH$_2$Cl$_2$ and 2 drops of pyridine were added. The solution was stirred for 27 hours. The reaction mixture was diluted with 30 mL of Et$_2$O and extracted with 5 mL of H$_2$O, 5 mL of 10% aqueous HCl, 5 mL of H$_2$O, 5 mL of saturated NaHCO$_3$ solution, 5 mL of H$_2$O and 5 mL of brine, dried (Na$_2$SO$_4$) and concentrated. The crude solid was dried under reduced pressure: $^1$H-NMR (CDCl$_3$)δ7.66–7.35 (m, 28H), 6.15 (s, 1H), 6.13 (s, 1H), 3.78 (s, 3H), 3.75 (s, 3H), 3.70 (d, J=1.15 Hz, 3H), 3.56 (d, J=0.98 Hz, 3H).

The Mosher Ester of (R)-(−)-Methyl [(1.1'-Biphenyl)4-yl]-α-hydroxyacetate was prepared as described for the Mosher ester derivative of the racemic acetate: $^1$H-NMR (CDCl$_3$)δ7.66–7.31 (m, 14H), 6.13 (s, 1H), 3.78 (s, 3H), 3.70 (d, J=1.15 Hz, 3H).

The Mosher Ester of (S)-(+)-Methyl [(1,1'-Biphenyl)4-yl]-α-hydroxyacetate was prepared as described for the Mosher ester derivative of the racemic acetate: $^1$H-NMR (CDCl$_3$)δ7.61–7.35 (m, 14H), 6.15 (s, 1H), 3.75 (s, 3H), 3.56, (d, J=0.98 HZ, 3H).

EXAMPLE O (R)-(−)-Methyl [(1,1'-Biphenyl)4-yl]-α-((1,1-dimethylethyl)-dimethylsilyl)oxyacetate α-Hydroxyacetate (1.8 g; 7.5 mmol), 1.8 g (12.0 mmol) of TBDMSCl, 0.82 g (12.0 mmol) of imidazole and 10 mL of DMF were combined in a 100 mL round bottom flask and stirred under argon for 18 h. The reaction mixture was diluted with 150 mL of Et$_2$O, washed three times with 25 mL of H$_2$O and once with 25 mL of brine, dried (Na$_2$SO$_4$), and concentrated. The compound was dried under reduced pressure (0.3 mm Hg, 60°. C.) for 1.5 hours to yield 2.6 g (98%) of the title tert-butyldimethylsilyloxyacetate as a cloudy white oil: $\alpha_D^{22}$−71.9° (c=0.914, EtOH); $^1$H-NMR (CDCl$_3$)δ7.59–7.33 (m, 9H), 5.28 (s, 1H), 3.70 (s, 3H), 0.92 (s, 9H), 0.12 (s, 3H), 0.05 (s, 3H).

(S)-(+)]-Methyl [(1.1'-Biphenyl)4-yl]-α-((1,1-dimethylethyl)-dimethylsilyl)oxyacetate was prepared as described for the corresponding (R)-(−)-enantiomer from (S)-(+)-methyl p-phenylmandelate: $\alpha_D^{22}$+68.8° (c=0.780, EtOH).

EXAMPLE P (R)-(−)-[(1,1'-Biphenyl)4-yl]-α-((1,1-dimethylethyl)-dimethylsilyl)oxy-acetaldehyde A 100 mL 2-necked round bottom flask was equipped with a septum, N$_2$ inlet and 2.6 g (7.4 mmol) of the (R)-(−)-methyl acetate of Example O dissolved in 45 mL of dry toluene. The solution was cooled to −78° C. (CO$_2$/acetone), and 9 mL (9 mmol) of a 1.0M solution of DIBAL-H in toluene was added slowly (5 min.) with stirring. The reaction mixture was stirred for 1 h at −78° C. and poured into a mixture of 100 g of ice and 100 mL of CHCl$_3$. The reaction flask was rinsed with 100 mL of CHCl$_3$ and the mixture was stirred vigorously for 30 min. After separation of the CHCl$_3$ layer, the aqueous phase was washed with 100 mL of CHCl$_3$ (emulsion!) and the combined CHCl$_3$ extracts were washed once with brine 80 mL, dried (Na$_2$SO$_4$) and concentrated leaving 2.3 g (95%) of the title aldehyde as a colorless oil which was not further purified: $^1$H-NMR (CDCl$_3$)δ9.54 (d, J=2.1 Hz, 1H), 7.63–7.35 (m, 9H), 5.05 (d, J=2.1 Hz, 1H), 0.97 (s, 9H), 0.14 (s, 3H), 0.07 (s, 3H).

(S)-(+)-[(1,1'-Biphenyl)4-yl]-α-(1,1-dimethylethyl) dimethylsilyl)oxy-acetaldehyde was prepared from (S)-(+)-methyl α-silyloxymandelate as described for the corresponding (R)-(−)-enantiomer: $\alpha_D^{22}+36.6°$ (c=1.01, EtOH).

EXAMPLE Q

(R)-(−)-Methyl α-Hydroxybenzeneacetate

A solution of (R)-(−)-mandelic acid (1.52 g; 10 mmol) in 70 mL of Et$_2$O was cooled to 0° C. and titrated with CH$_2$N$_2$ until the yellow color persisted. Evaporation of solvent provided 1.65 g (99%) of the title methyl ester as a colorless oil which crystallized upon standing: m.p. 54°–55° C.

(S)-(+)-Methyl α-Hydroxybenzeneacetate was prepared as described for the corresponding (R)-(−)-enantiomer. The oil crystallized upon standing: m.p. 54°–56° C., $\alpha_D^{22}+125°$ (c=2.30, EtOH).

EXAMPLE R

(R)-(−)-Methyl α-[((1,1-Dimethylethyl)dimethylsilyl)oxy]-benzeneacetate

The α-Hydroxy acetate of Example Q (1.65 g; 10.0 mmol), 2.26 g (15.0 mmol) of TBDMSCl, 1.16 g (17.0 mmol) of imidazole and 12 mL of DMF were combined in a 100 mL round bottom flask and stirred under argon for 18 hours. The reaction mixture was diluted with 150 mL of Et$_2$O, washed three times with 25 mL of H$_2$O and once with 25 mL of brine, dried (Na$_2$SO$_4$) and concentrated. The compound was dried under reduced pressure (0.3 mm Hg, 60° C.) for 1.5 hours to yield 2.8 g (99%) of the title tertbutyldimethylsilyl-oxyacetate as a colorless oil: $\alpha_D^{22}-53.6°$ (c=1.25, EtOH); $^1$H-NMR (CDCl$_3$)δ7.47–7.27 (m, 5H), 5.22 (s, 1H), 3.67 (s, 3H), 0.90 (s, 9H), 0.09 (s, 3H), 0.02 (s, 3H).

(S)-(+)-Methyl α-[((1,1-Dimethylethyl)dimethylsilyl)oxy]-benzeneacetate was prepared as described for the corresponding (R)-(−)-enantiomer: $\alpha_D^{22}+57.4°$ (c=0.592, EtOH).

EXAMPLE S

(R)-(−)-α-[((1,1-Dimethylethyl)dimethylsilyl) oxy]benzeneacetaldehyde

To a 100 mL 2-necked round bottom flask equipped with a septum and nitrogen inlet was added 2.8 g (10 mmol) of the (R)-(−)-methyl acetate of Example R dissolved in 55 mL of dry toluene. The solution was cooled to −78° C. (CO$_2$/acetone) and 12 mL (12 mmol) of a 1.0M solution of DIBAL-H in toluene was added slowly (5 minutes) with stirring. The reaction mixture was stirred for 1 hour at −78° C. and poured into 100 g of ice and 100 mL of CHCl$_3$. The reaction flask was rinsed with 100 mL of CHCl$_3$ and the mixture was stirred vigorously for 30 minutes. After separation of the CHCl$_3$ layer, the aqueous phase was washed with 100 mL of CHCl$_3$ (emulsion) and the combined CHCl$_3$ extracts were washed with 80 mL brine, dried (Na$_2$SO$_4$) and concentrated leaving 2.2 g (88%) of aldehyde as a clear colorless oil of greater than 90% purity ($^1$H-NMR). The aldehyde was not further purified: $\alpha_D^{22}-39.5°$ (c=0.612, EtOH); $^1$H-NMR (CDCl$_3$)δ9.51 (d, J=2.2 Hz, 1H), 7.40–7.29 (m, 5H), 5.00 (d, J=2.2 Hz, 1H), 0.95 (s, 9H), 0.12 (s, 3H) 0.04 (s, 3H).

(S)-(+)-α-[((1,1-Dimethylethyl)dimethylsilyl) oxy]-benzeneacetaldehyde was prepared as described for the corresponding (R)-(−)-enantiomer: $\alpha_D^{22}+39.6°$ (c=0.442, EtOH).

EXAMPLE 1

A. (4R)-(−)-Ethyl 2-Carboxylate-2-[β-(4-chlorophenyl)-α-((2,2-dimethyl)1-propanoyl)oxy-β-((1,1-dimethylethyl)dimethylsilyl)oxy]-1,3-dithiane A solution of 0.52 mL (3.3 mmol) of ethyl 1,3-dithiane-2-carboxylate in 10 mL of THF (freshly distilled from Na/benzophenone) under argon was cooled to −78° C. (CO$_2$/acetone) and 2.2 mL (3.3 mmol) of 1.5M LDA (solution in cyclohexanes) was added with stirring. The reaction mixture was removed from the dry ice bath for 10 minutes, cooled to −78° C. and stirred for 1 hour. A solution consisting of 0.85 g (3.0 mmol) of (R)-(−)-p-chlorophenyl-α-[(1,1-dimethylethyl)dimethylsilyl)oxy]-acetaldehyde, 2 mL of THF and 0.41 mL (3.3 mmol) of pivaloyl chloride was added dropwise. Stirring was continued for 2 hours at −78° C. and for 1 hour at room temperature. The reaction mixture was diluted with 100 mL of Et$_2$O and washed once with 20 mL of H$_2$O, twice with 20 mL of 5% aqueous HCl, once with 20 mL of H$_2$O and once with 20 mL of brine, dried (Na$_2$SO$_4$) and concentrated. Chromatography over silica gel (70–230 mesh) using EtOAc:Hexanes (0.5:9.5) provided 1.1 g (62%) of the title dithiane as a diastereomeric mixture in the ratio of (8.4:1.6) (integration of the benzyl protons at δ5.92 (major) and 5.83 (minor)). The major diastereomer crystallized from the oil upon standing 4 to 8 days: m.p. 88°–89° C.; IR (KBr, pellet) 2978, 2967, 2929, 2858, 1741, 1724, 1225, 1144, 1101, 1022, 858, 838 cm$^{-1}$; $^1$H-NMR (major diastereomer) (CDCl$_3$)δ7.32–7.15 (m, 4H) , 5.83 (d, J=7.3 Hz, 1H), 5.11 (d, J=7.3 Hz), 4.18–4.04 (m, 2H —OCH$_2$CH$_3$), 3.26 (ddd, J=3.4, 10.5, 14.0 Hz, 1H) , 3.08 (ddd, J=3.2, 10.8, 14.0 Hz, 1H), 2.83–2.69 (m, 2H), 2.07–1.83 (m, 2H), 1.23 (t, J=7.2 Hz, 3H), 0.97 (s, 9H), 0.73 (s, 9H), 0.05 (s, 3H), −0.26 (s, 3H). Anal. calcd. for C$_{26}$H$_{41}$O$_5$SiS$_2$Cl; C, 55.64%, H, 7.36%; Found: C, 55.37; H, 7.63.

B. (4R)-(−)-Ethyl 4-(p-Chlorophenyl)-3-((2,2-dimethyl) 1-propanoyl)oxy)-4-((1,1-dimethylethyl)dimethylsilyl)oxy-2-oxobutanoate To a solution of 3.25 g (24.3 mmol) of N-chlorosuccinimide and 4.7 g (27.8 mmol) of AgNO$_3$ in 200 mL of CH$_3$CN:H$_2$O (8:2) was added a solution of 2.9 g (5.17 mmol) of the pivaloyl dithiane diastereomers prepared in Example 1A in 10 mL of acetone. The reaction mixture was stirred at room temperature for 25 minutes and quenched by the addition of the following at 1 minute intervals: 2 mL of saturated Na$_2$SO$_3$ solution, 2.0 mL of saturated Na$_2$CO$_3$ solution, 2.0 mL of brine and 200 mL of CH$_2$Cl$_2$:Hexanes (1:1). The organic layer was separated, washed once with 30 mL of brine, dried (MgSO$_4$) and concentrated. Filtration through silica gel using EtOAc:Hexanes (9.5:0.5) as elutant provided 2.0 g (82%) of the title α-keto ester as an 8.4:1.6 mixture of diastereomers (integration of $^1$H NMR for the benzylic protons at δ5.82 (minor) and 5.59 (major) in the form of a colorless oil: IR (NaCl plates) 2960, 2933, 2860, 1738, 1274, 1261, 1151, 1092 cm$^{-1}$; $^1$H-NMR (CDCl$_3$) for major diastereomer δ7.40–7.30 (m, 4H), 5.59 (d, J=8.0 Hz, 1H), 4.96 (d, J=8.0 Hz, 1H), 4.29 (q, J=7.1 Hz, 2H), 1.35 (t, J=7.1 Hz, 3H), 1.06 (s, 9H), 0.78 (s, 9H), −0.06 (s, 3H), −0.26 (s, 3H); Anal. calcd. for $C_{23}H_{35}O_6SiCl$: C, 58.64; H, 7.49: Found; C, 58.39; H, 7.55.

C.
(R)-(−)-5-(p-Chlorophenyl)3-((2,2-dimethyl)-1-propanoyl)oxy-4-hydroxy-2(5H)-furanone The (4R)-(−)-α-Keto ester of Example 1B (0.38 g; 0.8 mmol) was dissolved in 25 mL of THF and 1.0 mL (1.0 mmol) of a 1.0M solution of tetrabutylammoniumfluoride (TBAF) in THF was added dropwise with stirring. The solution turned green, then yellow, and after 10 minutes 5 mL of 10% aqueous HCl and 75 mL of $Et_2O$ were added. The $Et_2O$ layer was separated and washed once with 10 mL of 5% aqueous HCl solution, twice with 10 mL of $H_2O$ and once with 10 mL of brine, dried ($Na_2SO_4$) and concentrated in vacuo leaving 235 mg (94%) of the title tetronic acid: m.p 93°–95° C.; $\alpha_D^{22}$ −70.34° (c=0.118, EtOH); IR (KBr, pellet) 3700–2600 (broad, vinylogous acid), 1770, 1749, 1660, 1495, 1323, 1302, 1130, 1091, 1007 $cm^{-1}$; $^1H$ NMR ($CDCl_3$)δ7.45–7.30 (m, 4H), 5.65 (s, 1H), 1.35 (s, 9H); Anal. calcd. for $C_{15}H_{15}O_5Cl+\frac{1}{4}H_2O$; C, 57.15; H, 4.96: Found; C, 56.88; H, 5.08.

The (R)-(+)-Methylbenzylamine Salt of Racemic 5-(p-Chlorophenyl)-3-((2,2-dimethyl)-1-propanoyl)oxy)-4-hydroxy-2(5H)-furanone was prepared by dissolving 0.23 g (1.0 mmol) of p-chlorophenyl-2-hydroxytetronic acid in a mixture of 2 mL of pyridine, 2 mL of $CH_2Cl_2$ and 0.14 mL (1.1 mmol) of pivaloyl chloride under argon. The solution was stirred at room temperature for 12 hours followed by the addition of 1 mL of saturated $NaHCO_3$. After 1 hour the mixture was diluted with 20 mL of $Et_2O$ and extracted three times with 3 mL of $NaHCO_3$ solution. The aqueous layer was washed once with 5 mL $Et_2O$ and acidified with 10% HCl solution and extracted twice with 20 mL of $Et_2O$. The organic layer was washed once with 5 mL of 10% HCl solution, twice with 5 mL of $H_2O$ and once with 5 mL of brine, dried ($MgSO_4$) and concentrated leaving a white waxy solid. The racemic crude tetronic acid (0.015 g, 0.05 mmol) was dissolved in 0.75 mL of $CDCl_3$ containing 0.01 mL (0.1 mmol) of (R)-methylbenzylamine and 1 drop of $D_2O$. $^1H$ NMR ($CDCl_3$)δ7.36–7.27 (m, 22H (Note the extra 4 protons are from excess amine)), 5.20 (s, 1H ((R,R)-diastereomeric salt)), 5.11 (s, 1H ((S,R)-diastereomeric salt)), 3.98 (q, J=6.9 Hz, 2.5H (excess amine), 1.40 (d, J=6.9 Hz, 8H (excess amine)), 1.28 (s, 18H).

The (R)-(+)-Methylbenzylamine salt of (R)-(−)-5-(p-Chlorophenyl)-3-((2,2-dimethyl)-1-propanoyl)oxy-4-hydroxy-2(5H)-furanone was prepared by mixing 0.015 g (0.05 mmol) of (R)-(−)-5-(-chlorophenyl)-((2,2-dimethyl)-1-propanoyl)oxy)-4-hydroxy-2(5H)-furanone in 0.75 mL of $CDCl_3$, 0.01 mL (0.1 mmol) of (R)-methylbenzylamine and 1 drop of $D_2O$. $^1H$ NMR ($CDCl_3$)δ7.36–7.27 (m, 9H (2 additional protons were from excess amine)), 5.20 (s, 1H), 3.98 (q, J=6.9 Hz, 1.2H (excess amine), 1.40 (d, J=6.9 Hz, 4H (excess amine)), 1.28 (s, 9H).

The (R)-(+)-Methylbenzylamine Salt of (S)-(−)-5-(p-Chlorophenyl)-3-((2,2-dimethyl)-1-propanoyl)oxy-4-hydroxy-2(5H)-furanone was prepared by mixing 0.018 g (0.06 mmol) (S)-(+)-5-(-chlorophenyl)-((2,2-dimethyl)-1-propanoyl)oxy)-4-hydroxy-2(5H)-furanone in 0.75 mL of $CDCl_3$ and 0.02 mL (0.2 mmol) of (R)-methylbenzylamine. $^1H$ NMR ($CDCl_3$)δ7.33–7.19 (m, 19H (excess amine)), 5.13 (s, 1H), 4.30 (s, 7H ($RNH_3$+excess amine)), 3.99 (q, J=6.7, 3H (excess amine)), 1.34 (d, J=6.7, 9H (excess amine), 1.24 (s, 9H).

D.
(R)-(−)-p-Chlorophenyl-2,3-dihydroxy-2(5H)-furanone:

The pivaloyl tetronic acid prepared in Example 1C (165 mg, 0.53 mmol) and 10 mL of $AcOH$:$H_2O$ (9.8:0.2) were combined with stirring and warmed to c.a. 100° C. for 24 hours. The stir bar was removed and rinsed with 2 mL of iPrOH and the yellow solution was concentrated leaving an oil that was crystallized by warming on a steam bath and adding 2 mL of $CHCl_3$ and 1 mL of hexanes. The flask was allowed to cool slowly to room temperature and subsequently at 0° C. for 3 hours, filtered and washed with small portions of $CHCl_3$:hexanes (1:1) to yield 50 mg of optically pure (R)-(−)-p-chlorophenyl-2,3-dihydroxy-2(5H)-furanone. The mother liqueur was concentrated on a steam bath and diluted with hexanes until the solution became slightly turbid. Upon cooling, an additional 20 mg of product was isolated to yield a total of 70 mg (58%) of the title acid: m.p 173°–176° C. (dec.); $\alpha_D^{22}$ −128° (c=0.24, EtOH); $^1H$ NMR ($CD_3COCD_3$)δ7.48–7.37 (m, 4H), 5.69 (s, 1H).

The (R)-(+)-Methylbenzylamine Salt of Racemic 5-(p-Chlorophenyl)-3,4-dihydroxy-2(5H)-furanone was prepared by dissolving 12 mg (0.05 mmol) of the racemic 2-hydroxytetronic acid in 0.8 mL of $CDCl_3$. The initial suspension was taken into solution by the addition of 0.01 mL (0.1 mmol) of (R)-(+)-methylbenzylamine. The $^1H$ NMR spectrum of the sample was taken immediately before crystallization. Separation of the diastereomeric benzylic protons was best observed after addition of $D_2O$, but addition of $D_2O$ also initiates crystallization: $^1H$-NMR ($CDCl_3$)δ7.28–7.02 (m, 20H (excess amine)), 6.23 (br s, 12H ($RNH_3$+excess amine)), 4.96 (s, 1H), 4.91 (s, 1H), 3.77 (q, J=6.8 Hz, 2.5H (excess amine), 1.22 (d, J=6.8 Hz, 7H (excess amine)).

The (R)-(+)-Methylbenzylamine Salt of (R)-(−)-5-(p-Chlorophenyl)-3,4-dihydroxy-2(5H)-furanone was greater than 98% de by $^1H$ NMR analysis. (R)-(−)-2-hydroxytetronic acid (12 mg; 0.05 mmol) was dissolved in 0.8 mL of $CDCl_3$ containing 0.01 mL (0.1 mmol) of (R)-(+)-methylbenzylamine and 1 drop of $D_2O$: $^1H$ NMR ($CDCl_3$)δ7.28–7.02 (m, 9H), 4.93 (s, 1H), 3.92 (br q, J=6.8 Hz, 1H), 1.27 (d, J=6.8 Hz, 3H).

EXAMPLE 2

A. (4S)-(+)-Ethyl 2-Carboxylate-2-[β-(4-chlorophenyl)-α-((2,2-dimethyl)1-propanoyl)oxy-β-((1,1-dimethylethyl)dimethylsilyl)oxy]-1,3-dithiane was prepared by a procedure identical to that described for the synthesis of the corresponding (R)-(−)-enantiomer. The mixture of diastereomers that formed (8.4:1.6) was not separated.

B. (4S)-(+)-Ethyl 4-(p-Chlorophenyl)-3-((2,2-dimethyl)1-propanoyl)oxy)-4-((1,1-dimethylethyl) dimethylsilyl)oxy-2-oxobutanoate was prepared by a procedure identical to the one described for the corresponding (4R)-(−)-enantiomer.

C. (S)-(+)-5-(p-Chlorophenyl)-3-((2,2-dimethyl)-1-propanoyl)oxy)-4-hydroxy-2(5H)-furanone was prepared by a procedure identical to the corresponding (R)-(−)-enantiomer. Recrystallization from $Et_2O$ and Hexanes provided a white powder: m.p. 104°–110° C.; $\alpha_D^{22}$+85° (c=1.312, EtOH).

D. (S)-(+)-p-Chlorophenyl-2,3-dihydroxy-2(5H)-furanone was prepared by a procedure identical to the one described for the corresponding R-enantiomer: m.p. 165°–168° C. dec; $\alpha_D^{22}$ +105.4° (c=0.242, EtOH).

The (R)-(+)-Methylbenzylamine Salt of (S)-(+)-5-(p-Chlorophenyl)-3.4-dihydroxy-2(5H) -furanone was greater than 98% de by $^1$H NMR analysis. (S)-(+)-2-hydroxytetronic acid (12 mg; 0.05 mmol) was dissolved in 0.8 mL of CDCl$_3$ containing 0.02 mL (0.2 mmol) of (R)-(+)-methylbenzylamine. $^1$H NMR (CDCl$_3$)δ7.31–7.07 (m, 26H (excess amine)), 4.92 (s, 1H), 4.22 (s, 11H (RNH$_3$+excess amine)), 3.97 (q, J=6.7 Hz, 4H (excess amine)), 1.34 (d, J=6.7 Hz, 12H (excess amine)).

EXAMPLE 3

A. (4R)-(−)-Ethyl 2-[β-((1,1'-Biphenyl)4-yl)-α-((2,2-dimethyl)1-propanoyl)oxy-β-((1,1-dimethylethyl) dimethylsilyl)oxy]ethane-2-carboxylate-1,3-dithiane A solution of 0.52 mL (3.3 mmol) of ethyl 1,3-dithiane-2-carboxylate in 10 mL of THF (freshly distilled from Na/benzophenone) under argon was cooled to −78° C. (CO$_2$/acetone) and 2.2 mL (3.3 mmol) of 1.5M LDA (solution in cyclohexanes) was added with stirring. The reaction flask was removed from the dry ice bath for 10 minutes and subsequently cooled to −78° C. and stirred for 1 hour. A solution consisting of 0.98 g (3.0 mmol) of (R)-(−)-[1,1'-biphenyl)4-yl]-α-(1,1-dimethylethyl)dimethylsilyl)oxy-acetaldehyde, 2 mL of THF and 0.41 mL (3.3 mmol) of pivaloyl chloride was added drop-wise with stirring. Stirring was continued for 2 hours at −78° C. and for 1 hour at room temperature. The reaction mixture was diluted with 100 mL of Et$_2$O and washed once with 20 mL of H$_2$O, twice with 20 mL of 5% aqueous HCl, once with 20 mL of H$_2$O and once with 20 mL of brine, dried (Na$_2$SO$_4$) and concentrated. Chromatography over silica gel (70–230 mesh) using EtOAc:Hex (0.5:9.5) provided 1.1 g (62%) of the dithiane as a diastereomeric mixture in the ratio of (8.5:1.5) (integration of the benzyl protons at δ5.92 (major) and 5.65 (minor)). The diastereomers were separated by chromatography (major was slightly less polar) for analytical purposes; $^1$H-NMR (major diastereomer) (CDCl$_3$)δ7.57–7.30 (m, 9H), 5.92 (d, J=7.4 Hz, 1H), 5.18 (d, J=7.4 Hz, 1H), 4.20–4.04 (m, 2H —OCH$_2$CH$_3$), 3.27 (ddd, J=3.5, 10.4, 13.9 Hz, 1H), 3.09 (ddd, J=3.2, 10.7, 14.0 Hz, 1H), 2.83–2.72 (m, 2H), 2.07–1.83 (m, 2H), 1.29 (t, J=7.2 Hz, 3H), 0.95 (s, 9H), 0.75 (s, 9H), 0.07 (s, 3H), −0.22 (s, 3H). Anal. calcd. for C$_{32}$H$_{46}$O$_5$SiS$_2$; C, 63.76%, H, 7.69%. Found: C, 63.25;H, 7.64.

B. (4R)-(−)-Ethyl 4-[(1,1'-Biphenyl)4-yl]-3-((2,2-dimethyl)1-propanoyl)o-xy-4-((1,1-dimethylethyl) dimethylsilyl)oxy-2-oxobutanoate:

To a solution of 0.54 g (4.0 mmol) of N-chlorosuccinimide and 0.77 g (4.5 mmol) of AgNO$_3$ in 20 mL of CH$_3$CN:H$_2$O (8:2) was added a solution of 0.6 g (1.0 mmol) of the pivaloyl dithiane diastereomers prepared in Example 3A in 2 mL of acetone. The reaction mixture was stirred at room temperature for 25 minutes and quenched by the addition of the following at 1 minute intervals: 1 mL of saturated Na$_2$SO$_3$ solution, 1.0 mL of saturated Na$_2$CO$_3$ solution, 1.0 mL of brine and 80 mL of CH$_2$Cl$_2$:Hexanes (1:1). The organic layer was separated, washed twice with 20 mL of H$_2$O and once with 30 mL of brine, dried (MgSO$_4$) and concentrated. Filtration through silica gel using EtOAc:Hex (9.5:0.5) as elutant provided 0.36 g (70%) of the title α-keto ester as an 8.5:1.5 mixture of diastereomers (integration of $^1$H NMR for the benzylic protons at δ (minor) and 5.71 (major) in the form of a colorless oil: $^1$H-NMR (CDCl$_3$) for major diastereomer δ 7.63–7.35 (m, 9H), 5.71 (d, J=7.9 Hz, 1H), 5.06 (d, J =7.9 Hz, 1H), 4.31 (q, J=7.2 Hz, 2H), 1.37 (t, J=7.2 Hz, 3H), 1.10 (s, 9H), 0.82 (s, 9H), −0.01 (s, 3H), −0.20 (s, 3H); Anal. calcd. for C$_{29}$H$_{40}$O$_6$Si: C, 67.94; H, 7.86: Found: C, 67.67;H, 7.81.

C. (R)-(−)-5-[(1,1'-Biphenyl)4-yl]-3-((2,2-dimethyl)-1-propanoyl) oxy-4-hydroxy-2(5H) -furanone:

The (4R)-(−)-α-Keto ester prepared in Example 3B (0.35 g; 0.7 mmol) was dissolved in 20 mL of THF, and 0.8 mL (0.8 mmol) of a 1.0M solution of TBAF in THF was added dropwise with stirring. The reaction solution turned yellow, and after 10 minutes, 5 mL of 10% aqueous HCl and 75 mL of Et$_2$O were added. The Et$_2$O layer was separated and washed once with 10 mL of 5% aqueous HCl solution, twice with 10 mL of H$_2$O and once with 10 mL of brine, dried (Na$_2$SO$_4$) and concentrated in vacuo leaving 235 mg (94%) of the title tetronic acid. A sample was recrystallized as white plates from acetone and hexanes: m.p. 213°–220° C. dec.; $\alpha_D^{22}$ −82.3° (c=0.164, EtOH); IR (KBr, pellet) 2983, 2934, 1774, 1752, 1676, 1130, 1122, 1085 cm$^{-1}$; $^1$H NMR (CDCl$_3$)δ7.65–7.36 (m, 9H), 5.74 (s, 1H), 1.36 (s, 9H) ; Anal. calcd. for C$_{21}$H$_{20}$O$_5$ C, 71.58;H, 5.72: Found: C, 70.54;H, 4.75.

Optical Purity was Determined by $^1$H NMR of the Diastereomeric Salt of
(R)-(−)-5-[(1,1'-Biphenyl)4-yl]-3-((2,2 -dimethyl)-1-propanoyl)oxy-4-hydroxy-2(5H) -furanone with (R)-(+)-Methylbenzylamine.

The sample was prepared by mixing 0.015 g (0.05 mmol) of the acid in 0.75 mL of CDCl$_3$ and 0.01 mL (0.1 mmol) of (R)-methylbenzylamine: $^1$H NMR (CDCl$_3$)δ7.46–7.22 (m, 26H (excess amine)), 5.27 (s, 1H), 4.02 (q, J=6.7 Hz, 3.4H (excess amine)), 3.39 (br s, 11.6H (NH$_3$+excess amine)), 1.35 (d, J=6.7 Hz, 10H (excess amine)), 1.24 (s, 9H ).

D.
(R)-(−)-5-[(1,1'-Biphenyl)4-yl]-2,3-dihydroxy-2(5H)-furanone:

Method A: The pivaloyl tetronic acid prepared in Example 3C (180 mg, 0.50 mmol) and 10 mL of AcOH:-H$_2$O (9.8:0.2) were combined with stirring and warmed to c.a. 100° C. for 24 h. The stir bar was removed and rinsed with 2 mL of iPrOH and the yellow solution was concentrated leaving an oil that was crystallized from a mixture of CHCl$_3$ (2 mL) and hexanes (1 mL). The flask was allowed to cool slowly to room temperature and subsequently at 0° C. for 3 hours, filtered and washed with small portions of CHCl$_3$:hexanes (1:1) to yield 50 mg of optically pure 2-hydroxytetronic acid. The mother liquor was concentrated on a steam bath and diluted with hexanes until the solution became slightly turbid. Upon cooling, an additional 20 mg of product was isolated to yield a total of 70 mg (52%) of the title tetronic acid: m.p 207°–210° C. (dec); $\alpha_D^{22}$ −154° (c=0.13, EtOH) 1H NMR (DMSO-d$_6$)δ7.72–7.65 (m, 4H), 7.50–7.34 (m, 5H), 5.76 (s, 1H), 3.35 (br s, 2H).

Method B: A suspension of 178 mg (0.50 mol) of pivaloyl tetronic acid prepared in Example 3C in 15 mL of toluene and 7 mL of $CH_2Cl_2$ was cooled to $-78°$ C. in a dry flask under $N_2$ atmosphere. To the suspension with rapid stirring was added 1.75 mL (1.75 mmol) of 1M DIBAL-H dropwise. After 30 minutes the reaction was removed from the ice bath for 5 minutes, cooled to $-78°$ C. and quenched by the addition of 3 mL of 10% aqueous HCl and 50 mL of $Et_2O$. The organic layer was washed with 1×30 mL of $H_2O$ and extracted with 2×30 mL of $NaHCO_3$ solution. The $NaHCO_3$ layer was washed with 1×30 mL of $Et_2O$, acidified with 10% aqueous HCl and extracted with 2×40 mL of $Et_2O$. The $Et_2O$/hexanes (1:1) provided 55 mg (41%) of pure 2-hydroxytetronic acid: m.p. 194°–202° C. (dec.); $\alpha^1 -168°$ (C=0.31, EtOH).

The Salt of Racemic 5-[(1,1'-Biphenyl)4-yl]-3,4-dihydroxy-2(5H) -furanone with (R)-(+) -Methylbenzylamine was prepared by diluting 12 mg (0.05 mmol) of the racemic 2-hydroxytetronic acid in 0.8 mL of $CDCl_3$. The suspension was taken into solution by the addition of 0.01 mL (0.1 mmol) of (R)-(+)-methylbenzylamine. The $^1H$ NMR spectrum was taken immediately and prior to crystallization. Addition of $D_2O$ resulted in sample crystallization within 2-4 min: $^1H$-NMR $(CDCl_3)\delta7.61–7.18$ (m, (excess amine)), 5.08 (s, 1H), 5.03 (s, 1H), 3.97 (q, J=6.7 Hz, (excess amine)), 3.84 (br s, ($NH_3$+excess amine)), 1.33 (d, J=6.7 Hz, (excess amine)).

The Salt of (R)-(—)-5-[(1,1'-Biphenyl)4-yl]-3,4-dihydroxy-2(5H)-furanone with (R)-(+)-Methylbenzylamine was determined to be greater than 98% de by $^1H$ NMR analysis. The sample was prepared as described for the preparation of the racemic salt: $^1H$ NMR $(CDCl_3)\delta7.58–7.25$ (m, 22H (excess amine)), 5.69 (br s, 7H ($NH_3$+excess amine)), 4.98 (s, 1H), 3.96 (q, J=6.7 Hz, 2H (excess amine)), 1.34 (d, J=6.7 Hz, 7H (excess amine)).

EXAMPLE 4

A. (4S)-(+)-Ethyl 2-[β-(1,1'-Biphenyl)4-yl)-α-((2,2-dimethyl)1-propanoyl)oxy-β-((1,1-dimethylethyl)dimethylsilyl)oxy]ethane-2-carboxylate-1,3-dithiane was prepared by a procedure identical to that described for the synthesis of (R)-(—)-enantiomer in Example 3A. The mixture of diastereomers that formed (8.5:1.5) was not separated.

B. (4S)-(+)-Ethyl 4-[(1,1'-Biphenyl)4-yl]-3-((2,2-dimethyl) 1-propanoyl)oxy-4-((1,1-dimethylethyl) dimethylsilyl)oxy-2-oxobutanoate was prepared by a procedure identical to the one described in Example 3B for the (4R)-(—)-enantiomer.

C. (S)-(+)-5-[(1,1'-Biphenyl)4-yl]-3-((2,2-dimethyl)-1-propanoyl)oxy-4-hydroxy-2(5H)-furanone was prepared by a procedure identical to the one used to prepare the (R)-(—)-enantiomer of Example 3C: m.p.210°–215° C. dec; $\alpha_D^{22}$+84.8° (c=0.466, EtOH).

D. (S)-(+)-5-[(1,1'-Biphenyl)4-yl]-2,3-dihydroxy-2(5H)-furanone was prepared by a procedure identical to the one described in Example 3D for (R)-(—)-enantiomer: m.p. 182°–187° C. dec.; $\alpha_D^{22}$+145° (c=0.11, EtOH).

The Salt of (S)-(+)-5-[(1,1'-Biphenyl)4-yl]-3,4-dihydroxy-2(5H)-furanone with (R)-(+)-Methylbenzylamine was determined to be greater than 98% de by $^1H$ NMR analysis. The sample was prepared as described for the racemic salt: $^1H$ NMR $(CDCl_3)\delta7.54–7.19$ (m, (excess amine)), 5.05 (s, 1H), 4.03 (q, J=6.6 Hz), 3.28 (br s, $NH_3$+excess amine), 1.35 (d, J=6.6 Hz).

EXAMPLE 5

A. (4R)-(—)-Ethyl 2-Carboxylate-2-[α-((2,2-dimethyl)1-propanoyl)oxy-β-((1,1-dimethylethyl)dimethylsilyl)oxy-β-phenyl]-1,3-dithiane:

A solution of 1.58 mL (10.0 mmol) of ethyl 1,3-dithiane-2-carboxylate in 25 mL of THF (freshly distilled from Na/benzophenone) under argon was cooled to $-78°$ C. ($CO_2$/acetone) and 6.7 mL (10.0 mmol) of 1.5M LDA (solution in cyclohexanes) was added with stirring. The reaction mixture was removed from the dry ice bath for 10 minutes, cooled to $-78°$ C. and stirred for 1 hour. A solution consisting of 2.26 g (9.0 mmol) of (R)-(—)-1-[((1,1-dimethylethyl)dimethylsilyl)oxy]benzacetaldehyde 6 mL of THF and 1.25 mL (10 mmol) of pivaloyl chloride was added dropwise with stirring and stirring was continued for 2 hours at $-78°$ C. and for 1 hour at room temperature. The reaction mixture was diluted with 200 mL of $Et_2O$ and washed once with 20 mL of $H_2O$, twice with 20 mL of 5% aqueous HCl, once with 20 mL of $H_2O$ and once with 20 mL of brine. The organic layer was dried ($Na_2SO_4$) and concentrated. Chromatography over silica gel (70–230 mesh) using EtOAc:Hexanes (0.5:9.5) and distillation (0.3 mm Hg, 110° C.) to remove excess ethyl 1,3-dithiane-2-carboxylate provided 3 g (63%) of the title dithiane as an 8.3:1.7 mixture of diastereomers (integration of the benzylic protons at 5.92 (major) and 5.67 (minor)). An analytical sample of the pure major diastereomer was isolated by chromatography: IR (NaCl plates) 2960, 2929, 2904, 1729, 1279, 1250, 1215, 1140, 1113, 1093, 1057, 1030, 847, 838 $cm^{-1}$; $^1H$ NMR of the major isomer $(CDCl_3)\delta7.35–7.18$ (m, 5H), 5.92 (d, J=7.7 Hz, 1H), 5.11 (d, J =7.7 Hz, 1H), 4.22–4.08 (m, 2H ($-OCH_2CH_3$)), 3.33 (ddd, J=3.5, 10.5, 14.0 Hz, 1H), 3.09 (ddd, J=3.2, 10.8, 14.0 Hz, 1H), 2.86–2.71 (m, 2H), 2.10–1.86 (m, 2H), 1.32 (t, J=7.1 Hz, 3H), 0.96 (s, 9H), 0.73 (s, 9H), 0.06 (s, 3H), $-0.24$ (s, 3H); Anal. calcd. for $C_{26}H_{42}O_5SiS_2$; C, 59.29; H, 8.04. Found: C, 59.01; H, 7.28.

B. (4R)-(—)-Ethyl 4-Benzene-3-((2,2-dimethyl)1-propanoyl)oxy)-4-((1,1-dimethylethyl)dimethylsilyl)oxy-2-oxobutanoate:

To a solution of 0.54 g (4.0 mmol) of N-chlorosuccinimide and 0.77 g (4.5 mmol) of silver nitrate ($AgNO_3$) in 20 mL of acetonitrile:water (8:2) was added a solution of 0.53 g (1.0 mmol) of the pivaloyl dithiane diastereomers prepared in Example 5A in 2 mL of acetone. The reaction mixture was stirred at room temperature for 25 minutes and quenched by the addition of the following at 1 minute intervals: 1 mL of saturated $Na_2SO_3$ solution; 1.0 mL of saturated $Na_2CO_3$ solution; 1.0 mL of brine and 70 mL of $CH_2Cl_2$:Hexanes (1:1). The organic layer was separated, washed once with 15 mL of brine, dried ($MgSO_4$) and concentrated (note, it is essential that all solvent is removed prior to chromatography or excess succinimide will elute with compound). The crude product was diluted with EtOAc:hexanes (1: 9) and filtered through silica gel using EtOAc:Hexanes (9.5:0.5) as elutant to provide 0.30 g (70%) of the title α-keto ester as an 8.3:1.7 mixture of diastereomers (($^1H$ NMR) integration of the benzylic protons at $\delta5.72$ (minor) and 5.65 (major)) in the form of a colorless oil: IR (NaCl plates) 2960, 2931, 2860, 1736, 1271, 1259, 1153, 838 cm$^{-1}$; $^1$H-NMR (CDCl$_3$) for mixture δ7.41–7.25 (m, 6H (major and minor)), 5.71 (d, J=5.4 Hz, 0.2H (minor)), 5.66 (d, J=8.0 Hz, 1H (major)), 5.23 (d, J=5.4 Hz, 0.2H (minor)), 4.98 (d, J =8.0 Hz, 1H (major)), 4.28 (q, J=7.2 Hz, 2H (major)), 4.14 (q, J=7.2 Hz, 0.4H (minor)), 1.34 (t, J =7.2 Hz, 3H), 1.24 (t, J=7.2 Hz, 0.6H (minor)), 1.16 (s, 1.8H (minor)), 1.05 (s, 9H (major)), 0.84 (s, 1.8H (minor)), 0.78 (s, 9H (major)), 0.02 (s, 0.6H (minor)), 0.01 (s, 3H (major)), −0.02 (s, 0.6H (minor)), −0.04 (s, 3H (major)); Anal. calcd. for C$_{23}$H$_{36}$O$_6$Si: C, 63.27; H, 8.31: Found; C, 62.90; H, 7.60.

C.
(R)-(−)-5-Benzene-3-((2,2-dimethyl)-1-propanoyl)oxy-4-hydroxy-2(5H)-furanone

The (4R)-(−)-α-Keto ester prepared in Example 5B (0.28 g; 0.64 mmol) was dissolved in 20 mL of THF and 0.7 mL (0.7 mmol) of a 1.0M solution of tetrabutylammonium fluoride in THF was added dropwise with stirring. The reaction solution turned yellow, and after 10 minutes 5 mL of 10% aqueous HCl and 75 mL of Et$_2$O were added. The Et$_2$O layer was separated and washed once with 10 mL of 5% aqueous HCl solution, twice with 10 mL of H$_2$O and once with 10 mL of brine, dried (Na$_2$SO$_4$) and concentrated in vacuo leaving 170 mg (95%) of the title tetronic acid. An analytical sample was recrystallized from CHCl$_3$ and hexanes: m.p. 135°–138° C.; $\alpha_D^{22}$ −80.4° (c=0.734, EtOH); IR (KBr pellet) 3037, 2989, 2976, 2937, 2875, 2717, 1762, 1651, 1481, 1456, 1367, 1340, 1290, 1265, 1128, 1018, 771 cm$^{-1}$; $^1$H NMR (CDCl$_3$)δ7.42–7.39 (m, 5H), 5.69, (s, 1H), 1.35 (s, 9 H); Anal. calcd. for C$_{15}$H$_{16}$O$_5$; C, 65.21; H, 5.84: Found; C, 64.76; H, 5.62.

D. (R)-(−)-3,4-Dihydroxy-5-phenyl-2(5H)-furanone:

The pivaloyl tetronic acid of Example 5C (0.17 g, 0.62 mmol) and 10 mL of AcOH:H$_2$O (9.8:0.2) were combined with stirring and warmed to c.a. 100° C. for 24 hours. The stir bar was removed and rinsed with 2 mL of iPrOH and the yellow solution was concentrated leaving an oil that was crystallized by warming on a steam bath and adding 2 mL of CHCl$_3$ and 1 mL of hexanes. The flask was allowed to cool slowly to room temperature and subsequently at 0° C. for 3 hours. The crystalline solid was filtered and washed with small portions of CHCl$_3$:hexanes (1:1) to yield 50 mg of optically pure 2-hydroxytetronic acid. The mother liqueur was concentrated on a steam bath and diluted with hexanes until the solution became slightly turbid. Upon cooling, an additional 15 mg of product was isolated to yield a total of 65 mg (55%) of the tetronic acid: m.p.164°–170° C. (dec); lit racemic 155° C.; $\alpha_D^{22}$ −140° (c=0.546, EtOH).

The (R)-(+)-Methylbenzylamine Salt of (±)-3,4-Dihydroxy-5-phenyl-2(5H)-furanone was prepared by dissolving 12 mg (0.05 mmol) of the racemic 2-hydroxytetronic acid in 0.8 mL of CDCl$_3$. The initial suspension was taken into solution by the addition of 0.01 mL (0.1 mmol) of (R)-(+)-methylbenzylamine. The $^1$H NMR spectrum was taken immediately before crystallization took place. Better separation of the diastereomeric benzylic protons was observed after addition of D$_2$O, but D$_2$O initiates crystallization: $^1$H-NMR (CDCl$_3$)δ7.37–7.19 (m, 24H (diastereomeric mixture+excess amine)), 4.99 (s, 1H (diastereomer)), 4.96 (s, 1H (diastereomer)), 4.77 (br s, 7H (RNH$_3$+excess amine)), 3.70 (q, J=6.7 Hz, 3H (diastereomeric mixture+excess amine)), 1.18 (d, J=6.7 Hz, 8H (diastereomeric mixture+excess amine)).

The (R)-(+)-Methylbenzylamine Salt of (R)-(−)-3,4-Dihydroxy-5-phenyl-2(5H)-furanone was greater than 98% de by $^1$H NMR analysis. The (R)-(−)-2-Hydroxytetronic acid of Example 5D (12 mg; 0.05 mmol) was dissolved in 0.8 mL of CDCl$_3$ containing 0.01 mL (0.1 mmol) of (R)-(+)-methylbenzylamine: $^1$H NMR (CDCl$_3$)δ7.32–7.18 (m, 16H), 6.04 (br s, 6H(RNH$_3$+excess amine)), 4.88 (s, 1H), 3.84 (q, J=6.7 Hz, 2H (excess amine)), 1.26 (d, J=6.7 Hz, 6H (excess amine)).

EXAMPLE 6

A. (4S)-(+)-Ethyl 2-Carboxylate-2-[α-((2.2-dimethyl)1-propanoyl)oxy-β-((1,1-dimethylethyl)dimethylsilyl)oxy-β-phenyl]-1,3-dithiane was prepared by a procedure identical to that described in Example 5A for the synthesis of the (R)-(−)-enantiomer. The mixture of diastereomers that formed (8.3:1.7) was not separated.

B. (4S)-(+)-Ethyl 4-Benzene-3-((2,2-dimethyl)1-propanoyl)oxy)-4-((1,1-dimethylethyl)dimethylsilyl)oxy-2-oxobutanoate was prepared by a procedure identical to the one described in Example 5B for the (4R)-(−)-enantiomer.

C. (S)-(+)-5-Benzene-3-((2,2-dimethyl)-1-propanoyl)oxy)-4-hydroxy-2(5H)-furanone was prepared by a procedure identical to the one described for the (R)-(−)-enantiomer in Example 5C: m.p.136°–139° C., $\alpha_D^{22}$ +81.9° (c=0.804, EtOH).

D. (S)-(+)-3,4-Dihydroxy-5-phenyl-2(5H)-furanone was prepared by a procedure identical to the one described in Example 5C for the preparation of the R-enantiomer: m.p. 165°–170° C. dec. lit[29]. 142°–143° C.; $\alpha^{22}_{Na589}$+135° (c=0 512, EtOH) lit $\alpha_D^{22}$+109.4° (c=0.80; MeOH).[29]

The (R)-(+)-Methylbenzylamine Salt of (S),(+)-3,4-Dihydroxy-5-phenyl-2(5H)-furanone was in greater than 98% de by $^1$H NMR analysis. (S)-(+)-2-Hydroxytetronic acid (12 mg; 0.05 mmol) was dissolved in 0.8 mL of CDCl$_3$ and 0.02 mL (0.2 mmol) of (R)-(+)-methylbenzylamine. $^1$H NMR (CDCl$_3$)δ7.30–7.17 (m, 14H (excess amine)), 6.40 (br s, 6H (NH$_3$+excess amine)), 498 (s, 1H), 3.72 (q, J=6.7 Hz, 1.6H (excess amine)), 1.22 (d, J=6.7 Hz, 5H (excess amine )).

What is claimed is:

1. A process for the preparation of an optically pure compound of the formulae Ia or Ib:

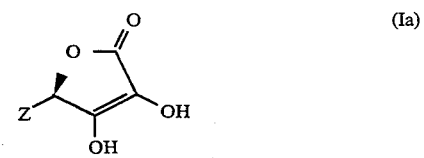

(Ia)

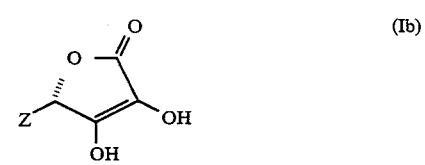

(Ib)

(a) reacting an optically pure aldehyde of the formula II

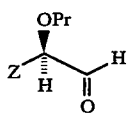
(II)

or its corresponding isomer, wherein Pr is a hydroxy protecting group selected from the group consisting of t-butyldimethylsily, tetrahydropyranyl, thiomethyl, and methoxymethyl, and Z is a substituted or unsubstituted aryl group;

with the anion of an alkyl 1,3-dithiane-2carboxylate followed by trapping of the intermediate alkoxide anion with a pivaloyl halide to yield a protected ester of the formula

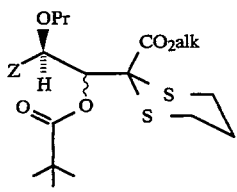
(III)

or its corresponding isomer, wherein Z and Pr are as hereinbefore defined and alk is a lower alkyl group;

(b) oxidatively hydrolyzing the protected ester of formula III to yield the α-keto ester of formula IV

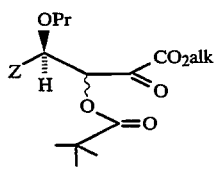
(IV)

or its corresponding isomer, wherein Z, Pr and alk are as hereinbefore defined;

(c) catalytically cyclizing the ester of formula IV to yield the 2-pivaloyloxytetronic acid derivative of formula V:

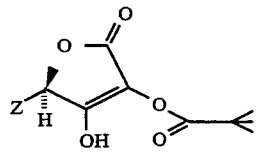
(V)

or its corresponding isomer, wherein Z and Pr are as hereinbefore defined; and (d) removal by hydrolysis or hydride reduction of the pivaloyl ester group to afford the desired optically pure 4-aryl-2-hydroxytetronic acid of either formula Ia or Ib.

2. The process according to claim 1 wherein the protecting group utilized in step (a) is t-butyldimethylsilyl.

3. The process according to claim 1 wherein the alkyl 1,3-dithiane-2-carboxylate used in step (a) is ethyl or methyl 1,3-dithiane-2-carboxylate.

4. The process according to claim 1 wherein the oxidative hydrolysis of step (b) is conducted using N-chlorosuccinimide and silver nitrate.

5. The process according to claim 1 wherein the cyclization of step (c) is induced with tetrabutylammonium fluoride.

6. The process according to claim 1 wherein the hydrolysis of step (d) is accomplished with acetic acid.

7. The process according to claim 1 wherein the pivolate cleavage is accomplished by selective hydride reduction using DIBAL-H.

8. The process according to claim 1 wherein the optically pure product prepared is (S)-(+)-5-(p-chlorophenyl)-3,4-dihydroxy-2(5H)-furanone.

9. The process according to claim 1 wherein the optically pure product prepared is (S)-(+)-5-[(1,1'-biphenyl)-4-yl]-3,4-dihydroxy-2(5H)-furanone.

10. The process according to claim 1 wherein the optically pure product prepared is (S)-(+)-3,4-dihydroxy-5-phenyl-2(5H)-furanone.

* * * * *